United States Patent
Hansen et al.

(10) Patent No.: US 7,928,211 B2
(45) Date of Patent: Apr. 19, 2011

(54) METHOD FOR PREPARING COMPOUNDS BY NUCLEIC ACID DIRECTED SYNTHESIS

(75) Inventors: Nils Jakob Vest Hansen, Copenhagen V (DK); Peter Blakskjaer, Arhus N (DK); Lars Kolster Petersen, Skaevinge (DK)

(73) Assignee: Vipergen Pharmaceuticals APS, Copenhagen (DK)

( * ) Notice: Subject to any disclaimer, the term of this patent is extended or adjusted under 35 U.S.C. 154(b) by 31 days.

(21) Appl. No.: 12/299,447

(22) PCT Filed: May 3, 2007

(86) PCT No.: PCT/DK2007/050054
§ 371 (c)(1),
(2), (4) Date: Feb. 12, 2009

(87) PCT Pub. No.: WO2007/124758
PCT Pub. Date: Nov. 8, 2007

(65) Prior Publication Data
US 2009/0239768 A1  Sep. 24, 2009

Related U.S. Application Data

(60) Provisional application No. 60/796,856, filed on May 3, 2006.

(51) Int. Cl.
*C07H 21/00* (2006.01)
*C07H 21/02* (2006.01)
*C12P 19/34* (2006.01)
*C40B 40/14* (2006.01)

(52) U.S. Cl. .................... 536/23.1; 536/24.3; 536/25.3; 506/16; 435/6; 435/91.1

(58) Field of Classification Search .................... 506/16; 536/23.1, 24.3, 25.3; 435/6, 91.1
See application file for complete search history.

(56) References Cited

FOREIGN PATENT DOCUMENTS

| WO | 0023458 A1 | 4/2000 |
| WO | 0061775 A1 | 10/2000 |
| WO | 02074929 A2 | 9/2002 |
| WO | 2004016767 A2 | 2/2004 |
| WO | 2004056994 A2 | 7/2004 |
| WO | 2006048025 A1 | 5/2006 |

OTHER PUBLICATIONS

M. Rozenman, et al, "DNA-Templated Synthesis in Organic Solvents," ChemBioChem, vol. 7, pp. 253-256, 2006.
K. Ijiro, et al, "A DNA-Lipid Complex Soluble in Organic Solvents," J. Chem. Soc., Chem. Commun., vol. 18, pp. 1339-1341, 1992.
K. Tanaka, et al, "A DNA-Lipid Complex in Organic Media and Formation of an Aligned Cast Film," Journal of the American Chemical Society, vol. 118, No. 44, pp. 10679-10683, 1996.
M. Alami, et al, "An Efficient Palladium-Catalysed Reaction of Vinyl and Aryl Halides or Triflates with Terminal Alkynes," Tetrahedron Letters, vol. 34, No. 40, pp. 6403-6406, 1993.
H. Borah, et al, "A Novel Indium-Catalyzed Sonogashira Coupling Reaction, Effected in the Absence of a Copper Salt, Phosphine Ligand and Palladium," SYNLETT, vol. 18, pp. 2823-2825, 2005.

(Continued)

*Primary Examiner* — Jezia Riley
(74) *Attorney, Agent, or Firm* — Sughrue Mion, PLLC

(57) ABSTRACT

The present invention provides compositions, compounds and methods for in vitro DNA display technology, allowing display of a variety of molecules, in particular molecules obtained by water incompatible mechanisms. Advantages of such methods are that combinatorial libraries can be constructed comprising molecules which are obtained through water incompatible reactions.

40 Claims, 12 Drawing Sheets

OTHER PUBLICATIONS

George P. Smith, "Filamentous Fusion Phage: Novel Expression Vectors That Display Cloned Antigens on the Virion Surface," Science, vol. 228, pp. 1315-1317, (Jun. 14, 1985).

J. Hanes, et al, "Ribosome display efficiently selects and evolves high-affinity antibodies in vitro from immune libraries," Proc. Natl. Acad. Sci. USA, vol. 95, pp. 14130-14135, (Nov. 1998).

M. Baca, et al, "Phage display of a catalytic antibody to optimize affinity for transition-state analog binding," Proc. Natl. Acad. Sci. USA, vol. 94, pp. 10063-10068, (Sep. 1997).

H. Pedersen, et al, "A method for directed evolution and functional cloning of enzymes," Proc. Natl. Acad. Sci. USA, vol. 95, pp. 10523-10528, (Sep. 1998).

S. Hart, et al, "Cell Binding and Internalization by Filamentous Phage Displaying a Cyclic Arg-Gly-Asp-containing Peptide," Journal of Biological Chemistry, vol. 269, No. 17, pp. 12468-12474, (Apr. 29, 1994).

M. Kanan, et al, "Reaction discovery enabled by DNA-templated synthesis and in vitro selection," Nature, vol. 431, pp. 545-549, (Sep. 30, 2004).

R. Roberts, et al, "RNA-peptide fusions for the in vitro selection of peptides and proteins," Proc. Natl. Acad. Sci. USA, vol. 94, pp. 12297-12302, (Nov. 1997).

Fructel, et al, Angewandte Chemie International Edition in English, vol. 35, No. 17, pp. 1879-1999, 1996.

"Addition to Carbon-Hetero Multiple Bonds," March's Advanced Organic Chemistry, 1992, 4th Ed., pp. 956-977.

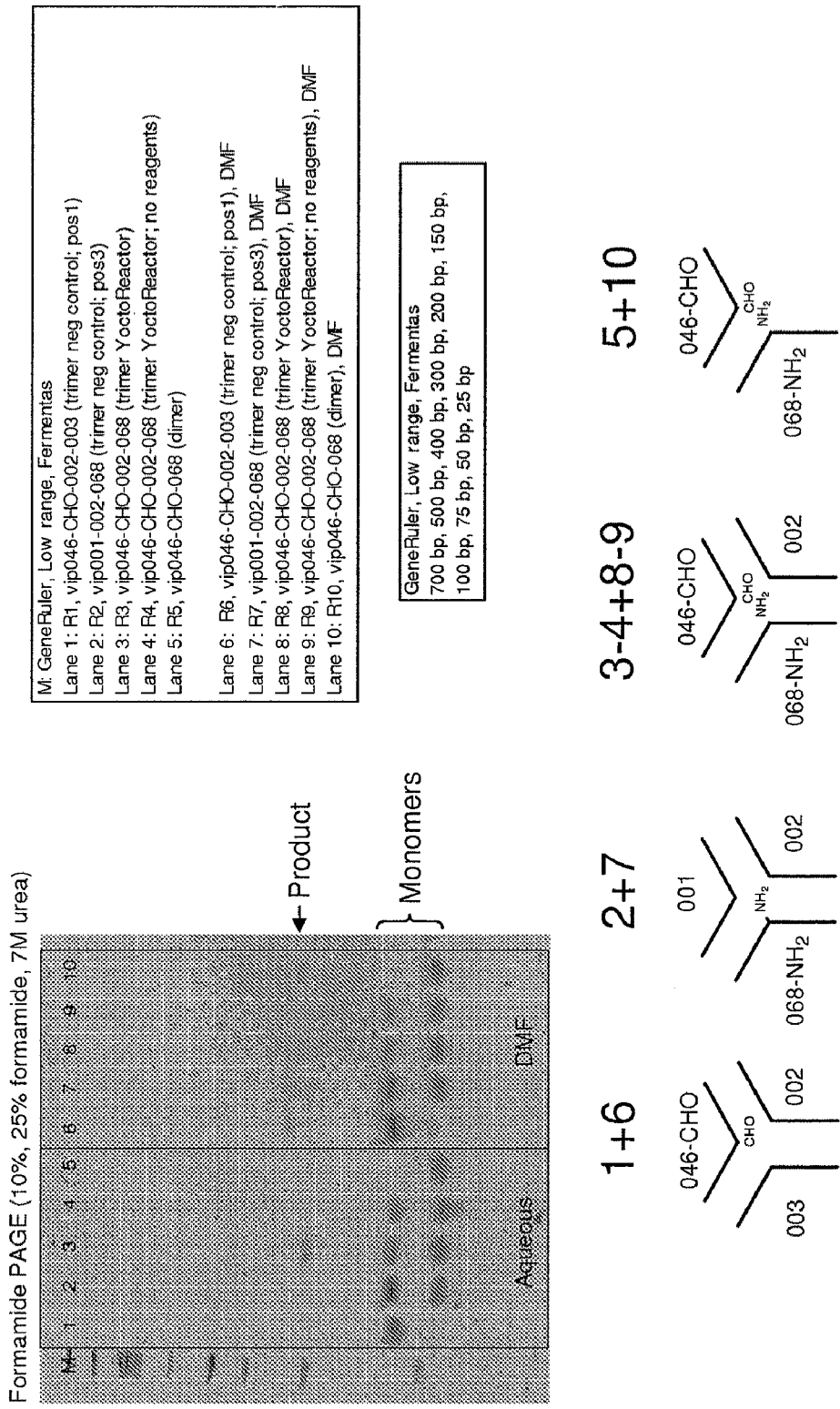
Figure 3 - reductive amination

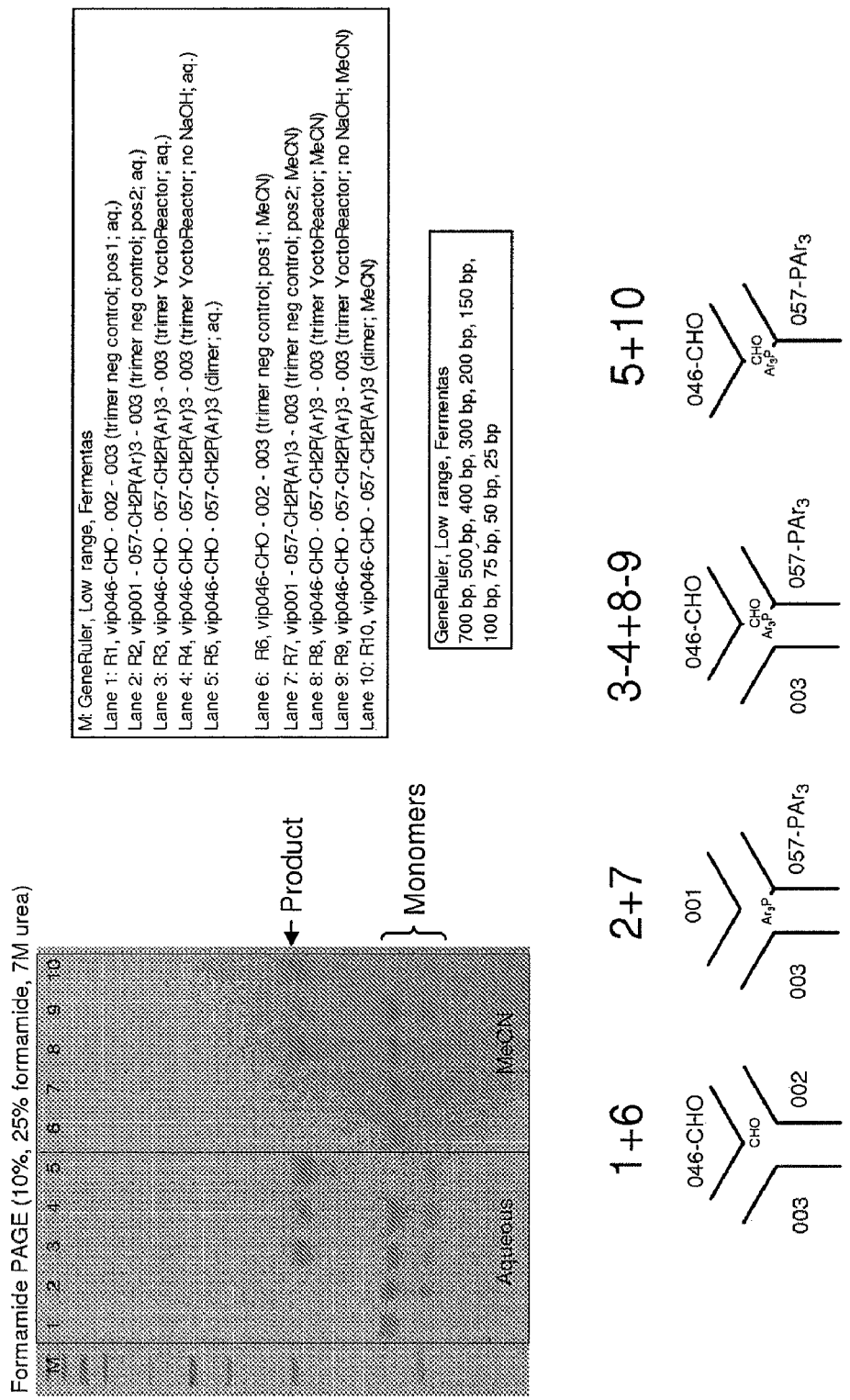
Figure 4 – Wittig reaction

Figure 5 – Aldol condensation
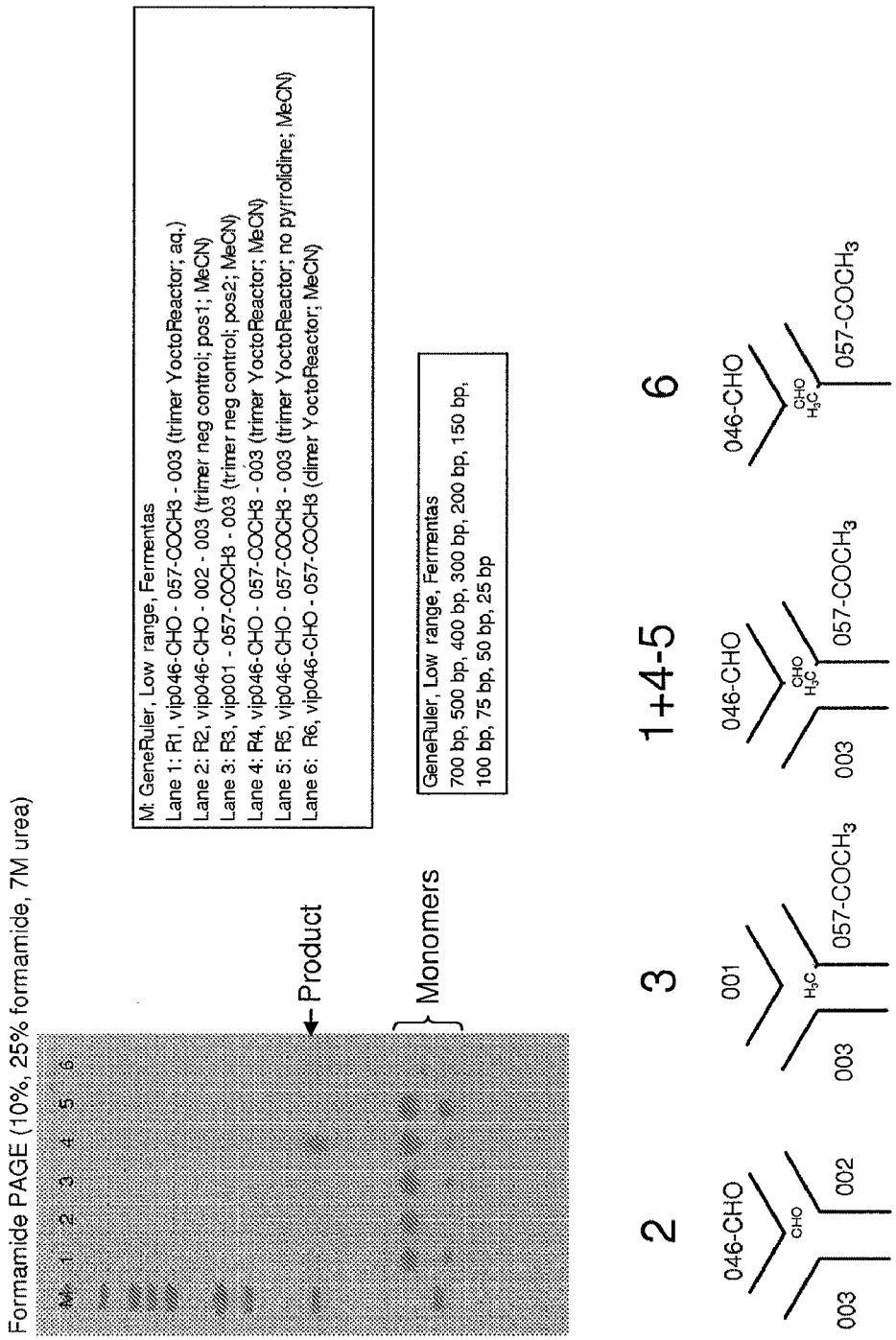

Figure 6 – Michael addition
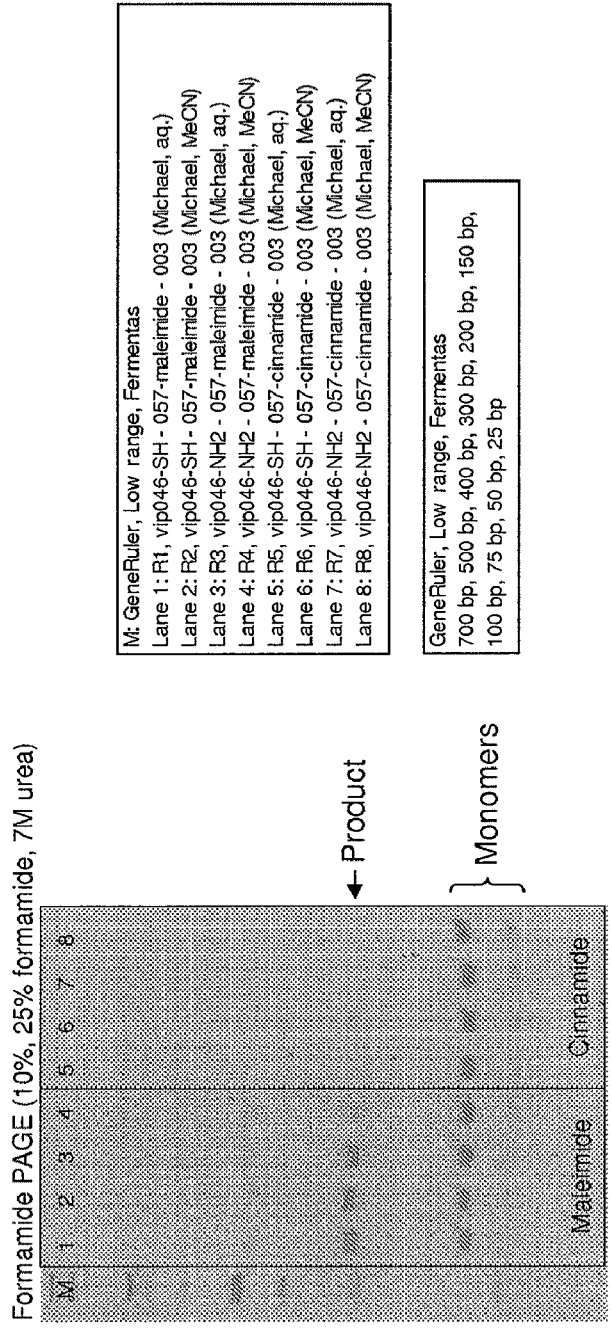
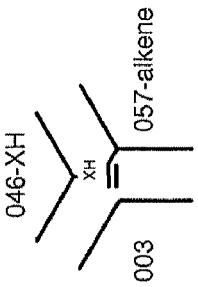

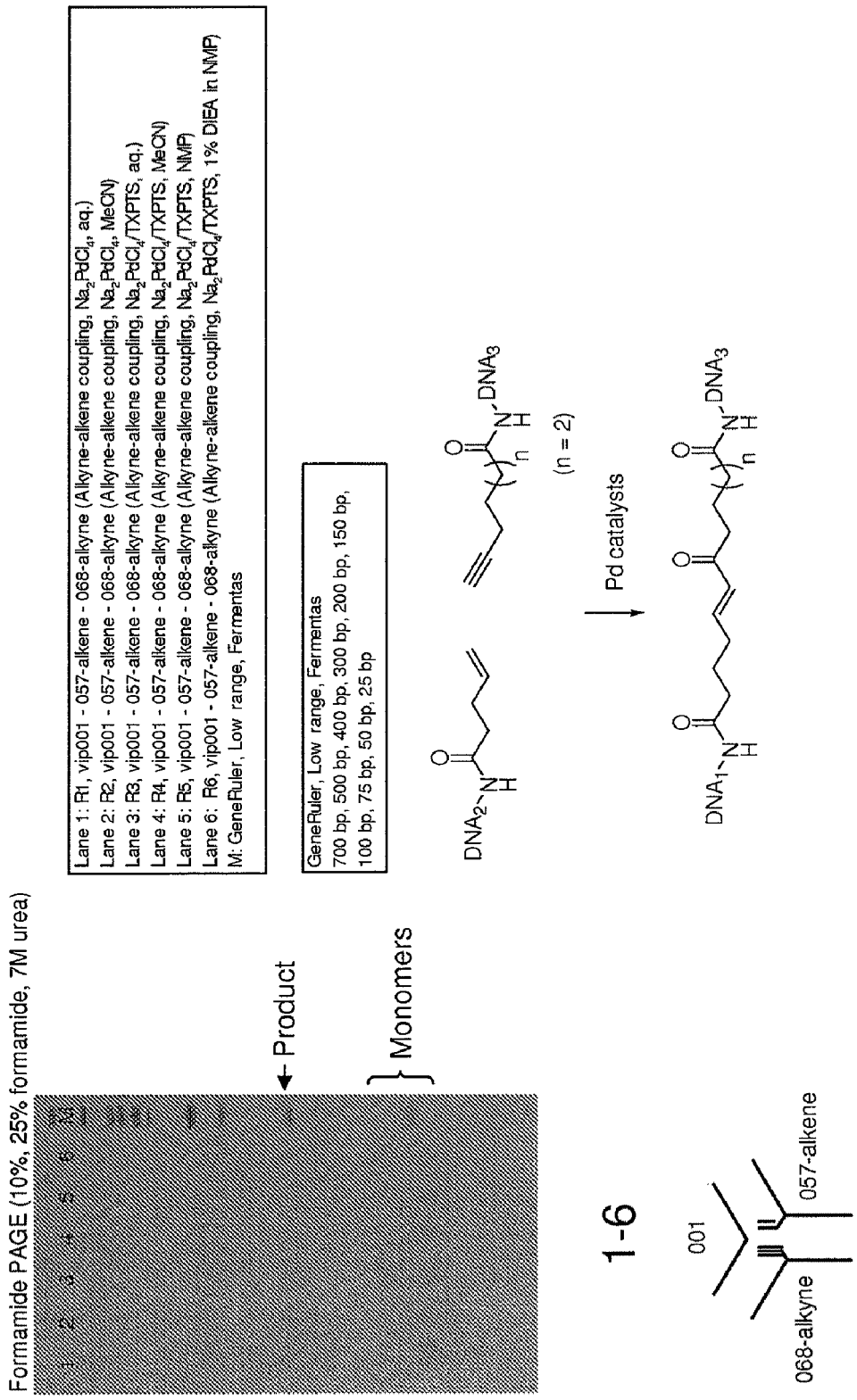
Figure 7 – Alkyne-alkene coupling

Figure 8 – Heck coupling
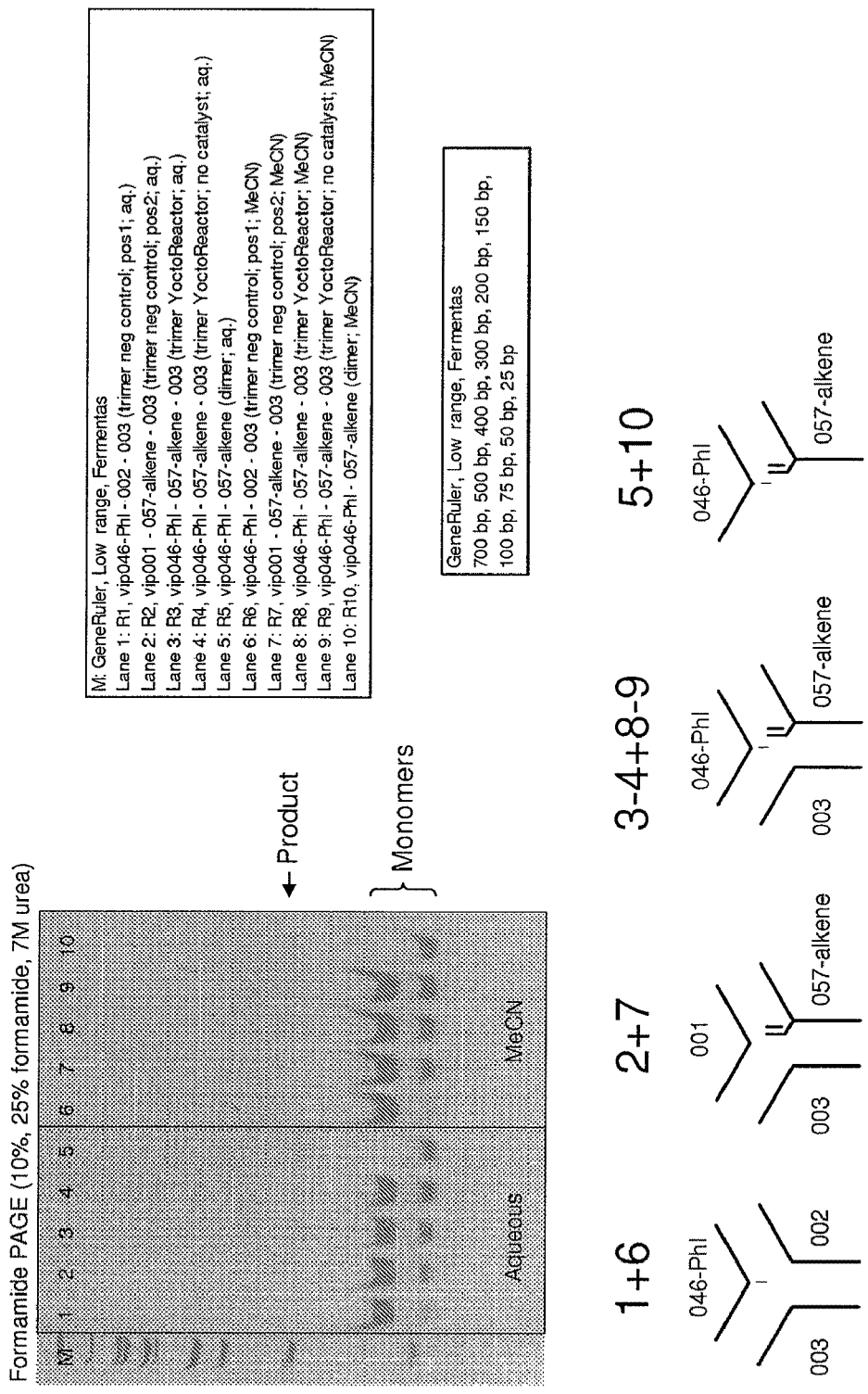

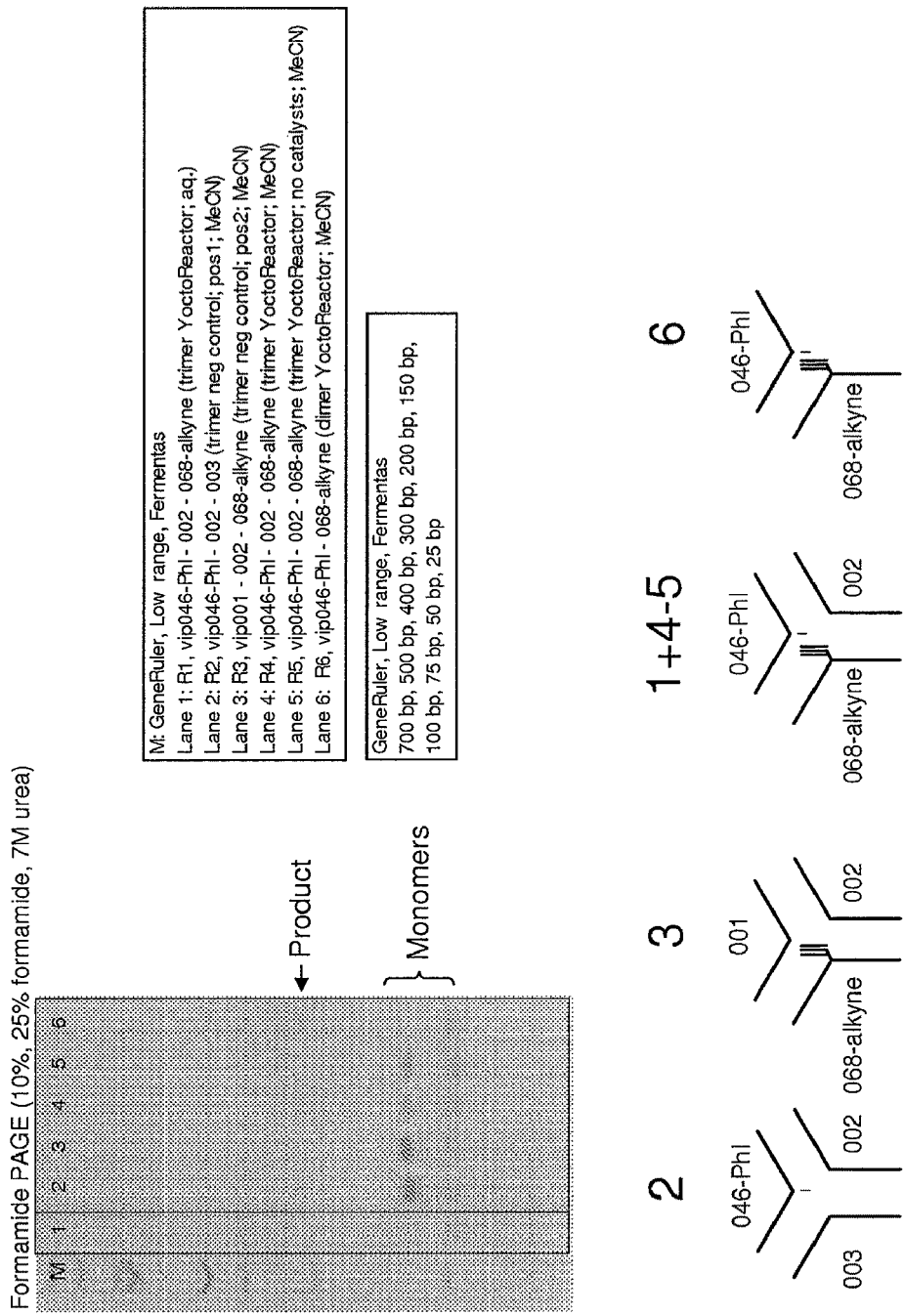
Figure 9 – Sonogashira coupling

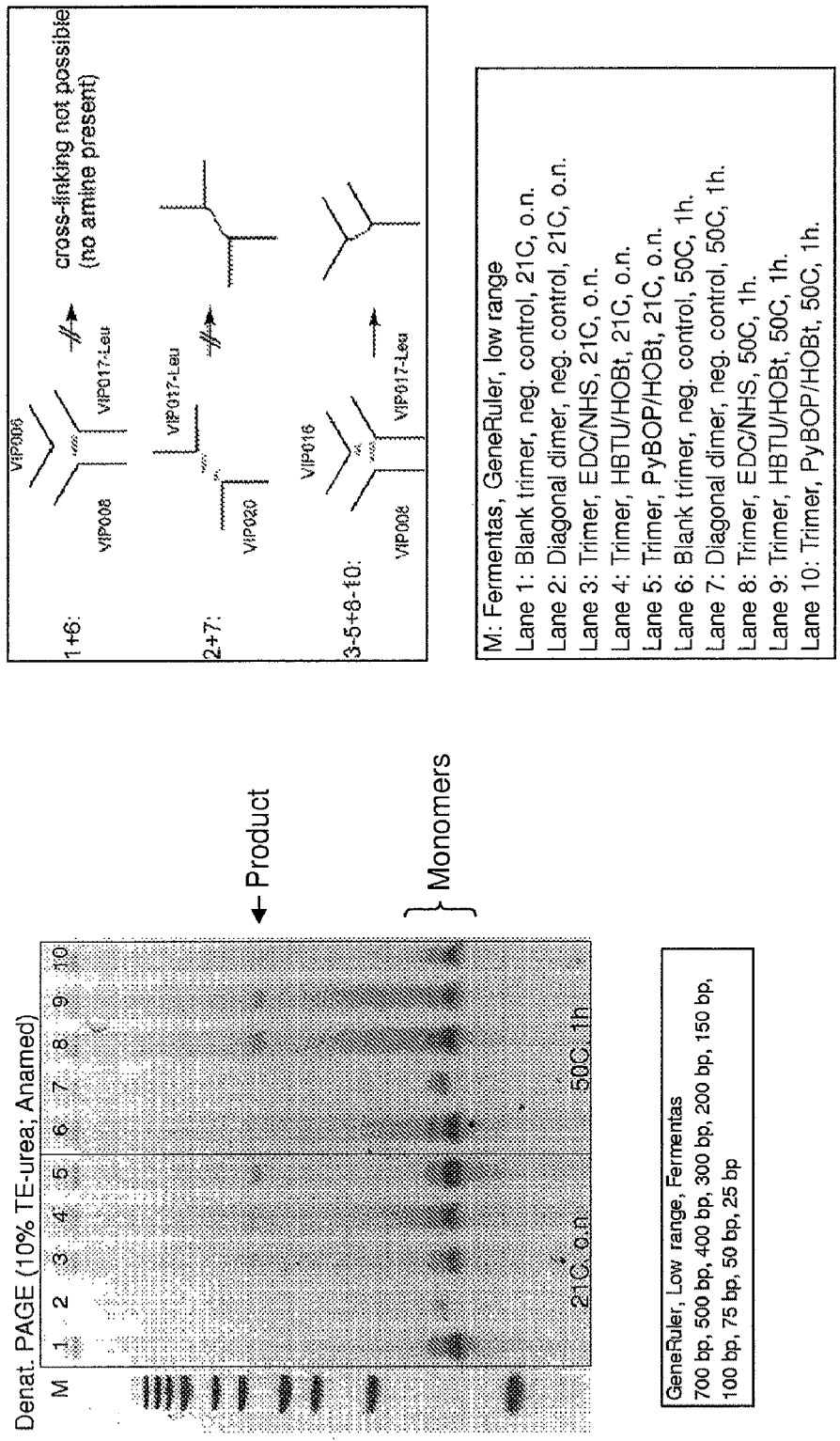
Figure 10 – Acylation in polyacrylamide pellets

SEQUENCE LISTING

<160> NUMBER OF SEQ ID NOS: 11

<210> SEQ ID NO 1
<211> LENGTH: 29
<212> TYPE: DNA
<213> ORGANISM: Artificial
<220> FEATURE:
<223> OTHER INFORMATION: oligonucleotide

<400> SEQUENCE: 1
accgactctg gaagtgtcac cggatctgg                                      29

<210> SEQ ID NO 2
<211> LENGTH: 29
<212> TYPE: DNA
<213> ORGANISM: Artificial
<220> FEATURE:
<223> OTHER INFORMATION: oligonucleotide

<400> SEQUENCE: 2
ccagatccgg tgactgtcaa ggctgaggt                                      29

<210> SEQ ID NO 3
<211> LENGTH: 29
<212> TYPE: DNA
<213> ORGANISM: Artificial
<220> FEATURE:
<223> OTHER INFORMATION: oligonucleotide

<400> SEQUENCE: 3
acctcagcct tgactcttcc agagtcggt                                      29

<210> SEQ ID NO 4
<211> LENGTH: 41
<212> TYPE: DNA
<213> ORGANISM: Artificial
<220> FEATURE:
<223> OTHER INFORMATION: oligonucleotide

<400> SEQUENCE: 4
ctcgttttcg agaccgactc tggaagtgtc accggatctg g                        41

<210> SEQ ID NO 5
<211> LENGTH: 42
<212> TYPE: DNA
<213> ORGANISM: Artificial
<220> FEATURE:
<223> OTHER INFORMATION: oligonucleotide

<400> SEQUENCE: 5
gagggagagc ctcacctcag ccttgactct tccagagtcg gt                       42

<210> SEQ ID NO 6
<211> LENGTH: 41
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (27)..(27)
<223> OTHER INFORMATION: amine-C6-dT

<400> SEQUENCE: 6
ctcgttttcg agaccgactc tggaagngtc accggatctg g                        41

```
<210> SEQ ID NO 7
<211> LENGTH: 42
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (28)..(28)
<223> OTHER INFORMATION: amine-C6-dT

<400> SEQUENCE: 7
ttggaaaaac caaccagatc cggtgacngt caaggctgag gt                              42

<210> SEQ ID NO 8
<211> LENGTH: 42
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (28)..(28)
<223> OTHER INFORMATION: amine-C6-dT

<400> SEQUENCE: 8
acacaagaag tgtagaatgc gttctccnct tccagagtcg gt                              42

<210> SEQ ID NO 9
<211> LENGTH: 21
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (11)..(11)
<223> OTHER INFORMATION: amine-C6-dT

<400> SEQUENCE: 9
actctggaag ngtcaccgga t                                                    21

<210> SEQ ID NO 10
<211> LENGTH: 21
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (11)..(11)
<223> OTHER INFORMATION: amine-C6-dT

<400> SEQUENCE: 10
atccggtgac ngtcaaggct g                                                    21

<210> SEQ ID NO 11
<211> LENGTH: 21
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (11)..(11)
<223> OTHER INFORMATION: amine-C6-dT

<400> SEQUENCE: 11
cagccttgac ncttccagag t                                                    21
```

METHOD FOR PREPARING COMPOUNDS BY NUCLEIC ACID DIRECTED SYNTHESIS

CROSS REFERENCE TO RELATED APPLICATIONS

This application is a National Stage of International Application No. PCT/DK2007/050054 filed May 3, 2007, claiming priority based on U. S. Provisional Application No. 60/796,856 filed May 3, 2006, the contents of all of which are incorperated herein by reference in their entirety.

FIELD OF THE INVENTION

The present invention provides compositions, compounds and methods for in vitro DNA display technology, allowing display of a variety of molecules, in particular molecules obtained by water incompatible mechanisms. Advantages of such methods are that combinatorial libraries can be constructed comprising molecules, which are obtained through water incompatible reactions.

BACKGROUND

Creation of huge libraries of organic compounds, usable for e.g. drug screening, is a convenient and economical means for developing new pharmaceuticals. Two out of several ways of creating such libraries are traditional solid support synthesis and display technologies taking advantage of nucleic acid directed synthesis. Solid support synthesis has been the traditional means for creating huge libraries of compounds, such as peptides, poly-carbohydrates and small molecule organic compounds. Nucleic acid directed synthesis, on the other hand, provides a more efficient means for effectuating reactions by utilizing the willingness of complementary nucleic acid strands to hybridize and thus bringing the reactants into proximity to each other, thereby enhancing the rate of reaction.

Display technologies have been developed to combine information storage and amplification capabilities of nucleic acids with the functional activities of other compounds. These display technologies rely on an association between a functional entity and a nucleic acid sequence which is informative about the structure of the functional entity.

An advantage of such methods is that very large libraries can be constructed and probed for a desired activity of the functional entities. Library members having the desired activity can then be partitioned from library members not having the desired activity, thus creating an enriched library with a higher fraction of members having the desired activity. This process is called selection. The structures of the library members in the enriched library can then be identified by their cognate nucleic acid sequence, thus allowing identification even from minute amounts of material.

Nucleic acid directed synthesis suffers from some limitations, namely that the nucleic acids are incapable of hybridizing in predominantly organic solvents and that hybridization is not error free occasionally resulting in incorrect matching of strands.

The first mentioned limitation means that the nature of the reactions is limited to water compatible reactions. This excludes reactions involving reactants that are insoluble in water, i.e. the reactants will not be able to "meet" the compound attached to the nucleic acids and therefore the rate of reaction will be heavily compromised; and reactions that are inhibited by water or proceed through a water incompatible mechanism.

The other limitation has an impact when creating large libraries. Firstly, when improper matching occurs the duplex may not be stable enough in order for the reaction to occur. Furthermore, it is necessary to employ systems, which can be selected and amplified with a maximum accuracy in order to enrich and identify the potential drug candidates.

Rozenman and Liu (Mary M. Rozenman and Davis R. Liu; *DNA-Templated Synthesis in Organic Solvents*; ChemBioChem 2006 7, 253-256) describe a method for performing DNA-templated Synthesis (DTS) in organic solvents using short (10-30 bp) DNA-duplexes of various conformations, i.e. i) in a simple end-of-helix architecture with juxtaposed reactants, ii) in a long-distance end-of-helix architecture with ten intervening nucleotides between the hybridized reactants, iii) in the "omega" architecture, described in e.g. WO04/016767A2 below, with a five-base loop ($\Omega5$) and iv) with reactants linked to non-complementary (mismatched) oligonucleotides. Rozenman and Liu show that such short structures are capable of remaining hybridized when transferred from an aqueous solvent into an organic solvent (up to 99.9% (V/V)) without the use of quaternary ammonium salts. This finding is contrary to previous studies where it was believed that the presence of such salts, which associate with the DNA phosphates in order to stabilize the duplex, was necessary for retention of the DNA-duplex in organic solvents (See e.g. K. Ijiro, Y. Okahata, J. Chem. Soc. Chem. Commun. 1992, 18, 1339-1341 and K. Tanaka, Y. Okahata, J. Am. Chem. Soc. 1996, 118, 10679-10683).

Using this method Rozenman and Liu have performed, in an organic solvent, various chemical reactions, which either require reagents that are insoluble in water or proceed through water incompatible mechanisms. Rozenman and Liu show that proper matching of the oligonucleotides into duplexes is a prerequisite for the reactions to proceed. It is therefore of utmost importance to a successful reaction that a nucleic acid system is employed, which provides a high degree of proper matching.

Thus, it has been shown that it is indeed possible to perform DNA templated synthesis in an organic solvent with short DNA duplexes when using the method of Rozenman and Liu. This method could be implemented in library construction technologies.

Similarly, in vitro display technologies taking advantage of the flexibility of organic chemistry and rounds of selections, amplification and diversification have been described. These methods rely on the use of templates.

One example is described in WO00/23458, using a "split and mix" principle a development of the conventional solid support synthesis. A library of ssDNA templates is used, each containing a chemical reaction site and several positions of codon segments. The templates are compartmentalized by virtue of hybridizing to a repertoire of anti-codon sequences for a given codon position. Then, a compartment specific chemical reaction is performed modifying the reaction site on the templates. The templates are then mixed and the process reiterated by using other codon positions to form a combinatorial library.

Another example is described in WO02/074929A2, using a "single-pot" principle. A library of oligonucleotide templates is used, each containing a chemical reaction site and several positions of codon segments. Furthermore, using a repertoire of transfer units, the method consists of an oligonucleotide anti-codon sequence and a chemical reactive group. The library of templates are hybridized with a repertoire of transfer units for a given codon position. This brings the chemical group on a hybridized transfer unit in proximity to the reaction site on the hybridized template, which consequently guides the chemical reaction of cognate pairs. This process is then reiterated using other codon positions to form a combinatorial library.

A limitation of the above proximity guiding of cognate pairs of code and chemical group is given by the linear structure of the template oligonucleotide. As a consequence of the linearity the distance between codon and the chemical reaction site will differ from codon position to codon position. For codon positions longer away from the reaction site the proximity guiding becomes compromised, as the local concentration drops to the power of three as a function of the distance. This disadvantage becomes more pronounced for complex libraries, with more codon positions and more complex codons.

This problem is sought solved in WO04/016767A2, where the transfer units apart from an anti-codon segment also contain a constant segment, which is complementary to a constant sequence on the template close to the reactive site. Thus, by hybridizing a transfer unit to a template, the template sequence between the codon position in question and the constant segment is bulging out, to form a so-called omega structure. The concept is that the codon segment is responsible for the specificity and the constant segment responsible for the proximity. Also suggested in WO04/016767A2 is a so-called T-architecture of the templates, where the reactive site on the template is situated in the middle of the template, with the codon positions spread out on each side. Consequently, the distance problem is so called "cut in half".

WO 2004/056994A2 discloses a method similar to WO02/074929A2 or WO04/016767A2 with the difference that the template is cut into minor sequences, termed "connecting polynucleotides" in the application. The connecting polynucleotides connect transfer units to bring these into reaction proximity. In certain embodiments the connecting polynucleotides may comprise a reactive chemical group. To obtain an encoded molecule the method is dependent upon codon/anti-codon recognition prior to reaction.

The template directed libraries described above are subsequently subjected to selections to form enriched libraries. The enriched libraries members' synthetic history can then be deduced through the encoding nucleic acid. The enriched libraries can also be amplified and diversified by for example error prone PCR, thus allowing for molecular evolution.

A limitation in these approaches is that a large number of templates have to be created, which is cumbersome, as the templates have to be of considerable length to ensure proper codon/anti-codon hybridization. In methods using a plurality of minor sequences to make up the final directed synthesis, the number of sequences to be synthesized is even higher than the actual library size.

The prior art methods using templates suffer from the disadvantage that the encoding is dependent upon hybridization of codon and anti-codon sequences. Sometimes hybridization between single stranded oligonucleotides will happen without perfect complementarities. In the case of library construction the result is loss of the association between the encoding and the synthetic history. Consequently, upon selection, positive codes may be de-selected and negative codes may be selected. For more complex libraries this disadvantage becomes more significant as the complexity of the single stranded oligonucleotides also increases, both with respect to numbers, length and sequences. This makes the processes more difficult to control As described above, in vitro display technologies allowing display of a variety of compound classes, selections, amplifications and diversifications have been developed. However, there is still an ongoing need for improvement, especially with respect to the quality in library construction and of diversification. The present invention offers a method for producing an encoded molecule in which the method does not require the pre-synthesis of a large number of templates or templates at all. Furthermore, the present method is not dependent upon codon/anti-codon recognition for an encoded molecule to be formed. Finally the present invention takes advantage of the establishment of a super nucleic acid structure prior to reaction, which allows for reaction of the chemical groups in a solvent predominantly consisting of an organic solvent.

SUMMARY OF THE INVENTION

The present invention relates to an in vitro display technology taking advantage of the flexibility of organic chemistry, especially organic chemistry that is incompatible with water, and permitting rounds of selection, amplification and diversification.

In particular, the present invention relates to a method for preparing compounds by nucleic acid directed synthesis comprising the steps of:
(i) Preparing an aqueous solution comprising a composition forming a star structure defining 3 or more stems extending from a reaction center, each stem being formed by a nucleic acid duplex, and at least 2 chemical groups being attached in or in the vicinity of the reaction center;
(ii) transferring the composition to a solution predominantly consisting of an organic solvent; and
(iii) providing, in the solution obtained in step (ii), conditions under which the at least 2 chemical groups will undergo reaction, thus providing a chemical compound.

It has surprisingly been found that such a star structure typically comprising, in the field of nucleic acid directed synthesis, relatively large nucleic acid duplexes formed in an aqueous solution and transferred to a predominantly organic solution will remain stably hybridized. Solutions predominantly consisting of an organic solvent are conditions under which single stranded nucleic acids would not be able to hybridize. Specifically, the star structure is (as reported herein) not able to hybridize in a solution containing e.g. more than 35% acetonitril or tetrahydrofuran or in more than 60% DMF.

The nucleic acid of the aqueous composition forms a super structure, in which different segments hybridize to each other so as to form a structure resembling a star. The star structure comprises a reaction center and a plurality of stems. In the reaction center, a chemical reaction can occur between the 2 or more chemical groups. The stems are nucleic acid duplexes, i.e. a stem comprises two hybridizing segments complementing each other sufficiently for a duplex to remain hybridized under conditions favoring the reaction of the chemical groups attached to the nucleic acids so as to form a chemical compound.

At least one of the stems extends radially from the center. Suitably, the 3 or more stems extend radially outwards from the reaction center. The duplex nucleic acid of the stems is believed to bring the chemical groups together so as to obtain reaction proximity. The proximity established between the chemical groups increases the local concentration and enhances the chances for a reaction to proceed.

The presence of 3 or more stems in the star structure creates a strong super structure, which is stable even at conditions where a single duplex will separate into two discrete single stranded nucleic acids. Thus, compared to the prior art systems typically comprising single duplexes, the structure of the invention will remain stably hybridized under more harsh conditions in respect of nucleic acid hybridization, i.e. in solvents disfavoring hybridization, high temperature and salt concentrations etc. In certain embodiments of the invention, the star structure encompasses 4, 5, 6, 7 or more stems connected to a mutual reaction center. When the number of stems is increased, the stability of the star structure is also increased, thus providing possibilities for applying even more harsh conditions. In a presently preferred embodiment the star structure encompasses 4 stems.

The number of stems present in the star structure has an impact on various factors. These factors are amongst others the number of single stranded nucleic acids that are necessary in order to obtain a library of a certain size having a divers constitution of compounds. Hence, when the number of stems increases the number of single stranded nucleic acids, necessary to be synthesized in order to obtain a certain size library, is reduced. Another factor is the size of the compound obtained by the reaction of the chemical groups. In order for a compound to be an effective drug for oral administration, the molecular weight of the compound should as a rule not exceed 500. Therefore, the star structure should not increase in the number of stems having a chemical group attached thereto so that the compound that will be formed exceeds 500. 4 stems will constitute a good balance between diversification of the library, the number of single stranded nucleic acids, the size of the compound obtained after reaction and the stability of the structure.

Thus, a reaction system for water incompatible organic synthesis is provided which is more stable and less error prone in respect of matching the correct nucleic acid strands. Furthermore, the amount of strands that need to be synthesized is reduced for any given size library and subsequent identification of reacted chemical groups is not dependent on codon/anti-codon hybridization, thus eliminating false positives and negatives when determining the nature of the compound formed during the reaction. The elimination of false positives/negatives secures a subsequently formed library of thousands of compositions from containing vast amounts of wrongly identified compositions, i.e. where positive compounds are deselected and negative compounds are selected.

The nucleic acid is segmented into various parts with certain functions. In certain aspects of the invention, the nucleic acid comprises one or more codons identifying the one or more chemical groups, which participate in the reaction. The presence of a codon segment makes it possible not only to use the nucleic acid to promote reaction proximity, but also to use the nucleic acid to code for one or more of the chemical groups which participated in the formation of the chemical compound. The presence of one or more codons is especially useful for decoding purposes. When the chemical compound formed according to the method of the invention is present in a small amount or is present in a mixture with other compounds, easy identification can be performed through molecular biological techniques.

A codon identifying a chemical group may be present anywhere in the nucleic acid forming the star structure, i.e. the codon may be present at or in the vicinity of the reaction center, in the hybridization segments or in other parts of the star structure. In a certain aspect of the invention a codon is situated at the extremity of a stem. A codon placed at the end of the stem pointing away from the center allows for more liberty in the design of the nucleic acid star structure as the codon at the extremity does not necessarily need for take part in the formation of a duplex or in the formation of the environment to the reaction center. The fact that the codon specifying the chemical reactant is an integral part of the nucleic acid also attached to the reactant for which it encodes and that the identification of that codon does not rely on hybridization with an anti-codon reduces the chance of erroneous hybridizations and thus false positive/negative identification of reactants of interest.

The stems may be blunt ended, sticky ended or a loop may be present. A blunt ended or sticky ended stem may be preferred when it is intended to ligate the stem to another nucleic acid. In a particular embodiment, a loop is present at all extremes of the stems except one, so as to form a contiguous nucleic acid sequence. Suitably, the contiguous sequence comprises a priming site to enzymatically extend the nucleic acid using a polymerase or another nucleic acid active enzyme. In appropriate instances the priming site is present at the stem not having a loop. Suitably, the nucleic acid comprises a priming site for a DNA polymerase, RNA polymerase or reverse transcriptase. Thus, the loops make it possible to prepare a double stranded extension product displaying the formed chemical compound.

In a preferred embodiment, the method of the invention further comprises the step (ia) between step (i) and step (ii) of providing in the solution obtained in step (i) conditions under which the at least 2 chemical groups will undergo reaction, thus providing a chemical compound.

This additional reaction step may serve at least two purposes. Firstly to maximize the turnover rate, i.e. maximize the product yield by allowing the reaction to occur both in an aqueous solution and subsequently in an organic solution. Another purpose is that a certain reaction may proceed through a two-step mechanism involving first aqueous and subsequently predominantly organic conditions. Providing this extra reaction step to the method is therefore a means for optimizing the overall reaction.

The reaction center and the stems may be unconnected or connected by any means such as covalent or non-covalent, but in a particular embodiment the reaction center and the stems are connected by means of joints extendable by an enzyme, preferably a polymerase, and in an even more preferred embodiment these joints are naturally occurring nucleic acids having a chemical group attached thereto, optionally by means of a linker. Having extendable joints, such as naturally occurring nucleic acids, connecting the stems and the reaction center is particularly useful when a subsequent extension and/or amplification reaction is to be performed.

The chemical groups present at or in the vicinity of the reaction center may in an embodiment be attached directly to the extendable joints. In another preferred embodiment, they are attached to the extendable joints by a linker. The purpose of this linker is to allow the chemical groups to come into reaction proximity. The linkers preferably have a length and composition to permit reactions between reactants paired by oligonucleotides, but yet minimizing reactions with unpaired entities. Another advantage of the linkers is that they may be easily cleaved from the star structure.

In a presently preferred embodiment, at least one of the chemical groups is attached via a linker that is not cleavable under conditions where the linker(s) attaching the remaining chemical group(s) is/are cleaved. Cleavage may be performed e.g. chemically or enzymatically, preferably chemically. Such a non-cleavable linker may e.g. only be cleavable under acidic conditions where the other linkers are cleaved under basic conditions and vice versa. Alternatively, an enzyme that does not cleave the non-cleavable linker will cleave the cleavable linker(s). Consequently, the formed chemical compound will after cleavage be attached to this at least one nucleic acid molecule.

When performing a subsequent extension reaction the formed chemical compound will be attached to the nucleic acid strand being extended as mentioned above. Thus, in a particular embodiment, the method of the invention further comprises the step of performing an enzymatic extension reaction to display the formed chemical compound.

Importantly, the extension product comprises a generally linear duplex, i.e. a complementing strand has been formed by the extension reaction. The extension reaction destroys the reaction center so the chemical compound previously formed by reaction in the reaction center is displayed in the media. The display of the chemical compound enables the use of various selection strategies on a library of extension products, as discussed later in this description.

Subsequent to the selection, the possibility of amplifying the nucleic acid is of particular relevance for identification purposes, because the chemical compound can be identified even in cases in which it occurs only in minute concentrations. The contiguous nucleic acid sequence suitably comprises codons of all the reactants, which has participated in the formation of the encoded chemical compound.

The transferal of the composition into a predominantly organic solvent may be effectuated simply by adding the solvent to the aqueous solution in a desired ratio for a specific reaction. Alternatively, a portion of the hybridized nucleic acid composition may be added to an organic solution. Both methods of transfer may be performed where appropriate, dependent on the nature of the reaction conditions.

In a particular embodiment the solution of step ii) is obtained by pouring an organic solvent to the aqueous solution obtained in step (i). Thus, the reaction mixtures only contain solvent and the aqueous solution. This simple dilution of the aqueous solution provides a reaction environment comprising a minimum of compounds not involved in the reaction to be performed. The advantage of this approach is that there will be no potential interference from compounds not intended for the reaction or even side reaction caused by these. In another embodiment, the solution may further comprise a solubilizer for the nucleic acid duplex. This may be necessary if the water content of the solution is approximately zero and the nucleic acid composition is not able to dissolve in the organic solution as such. This may particularly be necessary if the organic solution is completely immiscible with water. Importantly, it should be noticed that such a solubilizer should not be construed as a stabilizer of the nucleic acid composition. Therefore, in another preferred embodiment, the solution does not contain quaternary ammonium salts. It was previously believed that quaternary ammonium salts were necessary for maintaining and stabilizing the nucleic acid duplex when transferred into an organic solvent. However, when already hybridized, the super stable star structures of the method of the invention will remain stably hybridized even in a solution consisting substantially of organic matter. Furthermore, when quaternary ammonium salts are present there may be provided a slightly basic solution dependent on the concentration. This may prevent some reactions from being performed in the solution.

As previously mentioned, the type of reaction to be performed determines the nature of the solution predominantly consisting of an organic solvent. Thus, in a preferred embodiment, the solution in step ii) comprises more than 70% (V/V) of an organic solvent, in another preferred embodiment the solution comprises 70% to 99.9% (V/V) of an organic solvent. In yet another embodiment the solution comprises 70% to 99% (V/V) of an organic solvent, in another embodiment the solution comprises 90% to 99% (V/V) and in still another embodiment the solution comprises 90-95% or 95-99% (V/V) of an organic solvent, for example 70, 80, 90, 95, 99, 99.9% or ~100% (V/V) of an organic solvent.

The organic solvent may in an embodiment be miscible with water. Such water-miscible organic solvents may in a particular embodiment be acetonitrile, DMF, THF, dioxane, N-methylpyrrolidinone (NMP), dimethylacetamide (DMA), formamide, nitromethane, methanol, ethanol, propanol, tert-butanol, dimethylsulfoxide (DMSO), ethylene glycol, acetone, 2,2,2-trifluoroethanol (TFE), hexafluoro-2-propanol, sulfolane, 2-propanol, 1-butanol, 2-butanol, tetrahydropyran, nitroethane, 2-butanone, 2-methoxyethanol and ethylene glycol dimethyl ether, the solvent may similarly be a mixture of organic solvents where appropriate. In another embodiment the organic solvent may be immiscible with water. Such a water-immiscible solvent may be dichloromethane, chloroform, 1,2-dichloroethane, tetrachloromethane, toluene, benzene, ethyl acetate, propionitrile, diethylether, methyl tert-butyl ether (MTBE) and alkanes (e.g. pentane, hexane, heptane).

The reaction which the at least two chemical groups of step iii) undergo may in principle be any reaction. Preferred reactions are those involving a reactant that is not associated with the reaction center, the reactant being immiscible in water or reacting through a water-incompatible mechanism. The reaction may contemplate reactions that must be performed in a water insoluble solvent such as dichloromethane, DMSO, aliphatic carbohydrates etc. Furthermore the reaction may involve additional reactants not associated with the reaction center, such as catalysts that are insoluble in water; yet other reactions are those where water inhibits the reaction or causes an undesired side reaction to occur. Importantly, the method of the invention makes it possible to perform reactions that cannot be performed in an aqueous solvent. Therefore, the method of the invention expands the range of possible organic reactions to be performed using nucleic acid directed synthesis.

Presently preferred are reactions such as Wittig and related reactions, wherein the aldehyde or ketone may be aliphatic, alicyclic or aromatic, they may contain double and triple bonds and various functional groups; Aldol condensations, i.e. base catalyzed condensation reactions between two aldehydes, two ketones and/or an aldehyde/a ketone; Heck reactions, i.e. arylation or alkylation of olefins using organopalladium compounds; the reaction may be both inter- and intramolecular; alkyne-alkene oxidative coupling and reductive amination/reductive alkylation.

Other preferred reactions are Sonogashira coupling and Michael Addition. Sonogashira coupling is a reaction, which will not proceed in an aqueous solution, and is thus an example of the additional reactions that may be performed according to the method of the invention compared to the prior art. As compounds without chiral centers, such as those obtained in the Sonogashira coupling, are of particular interest in drug development, the possibility of performing reaction yielding such non-chiral compounds is of particular interest.

Michael Addition, another preferred reaction, is a frequently used reaction for adding functional groups to a double bond in the 1,4 position and sometimes to a triple bond situated either in straight chained or cyclic compounds.

When performing the reaction of step (iii) the conditions provided are dependent on the nature of the reaction to be performed, the list is not exhaustive, however, preferably such conditions are adjustment of pH, pressure, salt concentration and addition of further reactants not associated with the reaction center, i.e. reactants that are not one of the chemical groups.

In another preferred embodiment, at least one of the chemical groups attached in or in the vicinity of the reaction center is a chemical compound obtained by the method of the invention. Hence, one of the chemical groups may in a particular embodiment be the object of a previously conducted method according to the invention. Allowing the chemical group itself to be a product of a previous round of the inventive method allows for end products obtained through multiple step reactions conducted in a stepwise fashion. This may be necessary if the individual reactions are incompatible with each other, e.g. in respect of reaction conditions, reactants, solvents etc.

In yet another preferred embodiment, the chemical compound obtained in step (iii) is formed by means of 2 or more reaction steps. This embodiment is particular suitable when the line of reactions, which are necessary in order to obtain the chemical compound, are compatible with each other. The advantage of this embodiment is that only one round of reaction, extension etc. is necessary in order to obtain the chemical compound. In this embodiment, there will often be bound a chemical group to each stem. However, this is not a prerequisite since the compound may also be obtained using reactants not associated with the reaction center.

The chemical compound obtained in step (iii) is in a preferred embodiment attached to one extendable joint. Usually, one or more of the chemical groups are cleaved from the reaction center simultaneously with or subsequent to reaction thus resulting in the preferred compound that is only attached to one extendable joint. For a subsequent extension and amplification of the nucleic acid for the purpose of screening the compound as a potential drug candidate, it is important that the compound is attached to the nucleic acid. Otherwise, the compound would have to be recovered from the reaction mixture by more complicated means in order to test its potency as a drug. Furthermore, an unbound compound would be unsuitable for forming part of a library for the screening of multiple compounds.

In a second aspect the present invention provides a composition comprising a nucleic acid and at least 2 chemical groups attached to the nucleic acid, said composition forming a star structure defining 3 or more stems extending from a reaction center, each stem being formed of a nucleic acid duplex and the chemical groups being located in the reaction center and wherein the chemical group can only react in a solution predominantly consisting of an organic solvent.

Such a composition is usable as the composition in the method of the invention. The composition is due to the star structure being extremely stable and when transferred to a solution predominantly consisting of an organic solvent capable of remaining hybridized. This results in a reaction environment where the reactants are held into proximity to each other thus providing a high rate of reaction. The composition may in a preferred embodiment comprise 4 stems. 4 stems will as previously mentioned constitute a good balance between diversification of a library to be constructed, the number of single stranded nucleic acids, the size of the compound obtained after reaction and the stability of the structure.

The chemical groups to be reacted in the reaction center may be associated with the nucleic acid in any appropriate way. As an example, the chemical groups prior to reaction are covalently attached to the nucleic acid. Usually, one or more of the covalent attachments are cleaved simultaneously with or subsequent to reaction. The covalent link may be designed to be cleavable or durable. Furthermore, a cleavable linkage may be designed to be cleaved immediately upon reaction or designed to be cleaved in a step subsequent to a reaction.

In a third aspect is provided a composition comprising a nucleic acid and a chemical compound, said composition forming a star structure defining 3 or more stems extending from a reaction center, each stem being formed of a nucleic acid duplex, and the chemical compound has been formed in the reaction center as a product, the product being obtainable by reacting at least 2 chemical groups in a solution predominantly consisting of an organic solvent.

Thus a composition is provided which encompass chemical compounds not previously available for nucleic acid directed synthesis. Furthermore, the composition takes advantage of the super star structure, which ensures a more stable and less error prone structure in respect of matching the correct nucleic acid strands. Furthermore, the amount of strands that need to be synthesized is reduced for any given size library and subsequent identification of reacted chemical groups is not dependent on codon/anti-codon hybridization thus eliminating false positives and negatives when determining the nature of the compound formed during the reaction.

The composition may be obtained by the method of the invention.

In a preferred embodiment the chemical compound is covalently associated with at least one of the nucleic acid molecules. For a subsequent extension and amplification of the nucleic acid for the purpose of screening the compound as a potential drug candidate, it is important that the compound is attached to the nucleic acid. Otherwise the compound would have to be recovered from the reaction mixture by more complicated means in order to test its potency as a drug. Furthermore, an unbound compound would be unsuitable for forming part of a library for the screening of multiple compounds.

Usually, the chemical compound is formed by reaction of the chemical groups attached to the nucleic acid and optionally one or more further reactants. In a particular embodiment the reactants may originate from any source, including be a compound added to the reaction mixture as a free reactant not associated with a nucleic acid. The further reactant(s) may be scaffolds, cross-linking agents, activating agent, deprotecting agents, catalysts etc.

The star structures according to the present invention are as indicated above useful in the generation of libraries of different chemical compounds associated with a genetic code. Accordingly, the present invention also relates to a library of compositions comprising a plurality of compositions according to the invention. Similarly, in another aspect the present invention relates to a method for obtaining a library of compositions comprising collecting a plurality of compositions obtained by the method of the invention.

Each of the star structures may be present in several copies in the media and the media generally comprises star structures containing different chemical compounds. As an example, a library of the present invention may comprise at least 1000 different chemical compounds, preferably $10^6$ different chemical compounds, and more preferred $10^9$ different chemical compounds.

The library as described herein may be used to screen for a compound of interest. It is generally desired to have a library as large as possible to increase the possibility of finding a compound with desired properties. In a certain aspect of the invention, the property of the compound of interest is the ability to bind to a target. Generally, it is assumed that the possibility of finding a compound with high affinity and specificity towards a target is increasing with increasing library size. Thus, a library according to the present invention suitably comprises more than $10^3, 10^4, 10^5, 10^6, 10^7, 10^8, 10^9$, $10^{10}$, $10^{11}$, $10^{12}$, $10^{13}$, or $10^{14}$ different chemical compounds associated with a nucleic acid encoding the synthetic history.

The above-described aspects and embodiments show clear advantages over the prior art. To name some, the various possible embodiments of the present invention show one or more of the following advantages: 1) a method for assembly of a unique combinatorial display library, 2) a unique structure for proximity guiding of chemical reactions taking place in solutions predominantly consisting of an organic solvent, 3) the identification of the chemical reactions is highly independent of codon anti-codon recognition, 4) if accidentally an incorrect selection has occurred, the association between encoding and display will still exist as the fresh carrier modules provide both the chemical group and the code.

In still another aspect of the invention is provided a method for preparing compounds by nucleic acid directed synthesis comprising the steps of: (i) Preparing an aqueous solution comprising a composition forming a first stem of a star structure extending from a reaction center, the stem being formed by a nucleic acid duplex, wherein a chemical group is attached to each of the nucleic acid strands forming the duplex; (ii) providing conditions under which the 2 chemical groups undergo reaction, thus providing a chemical compound or intermediate; (iii) adding to the composition obtained in step (ii) a third nucleic acid strand forming at least a second stem of a star structure extending from a reaction center formed by a nucleic acid duplex, wherein a chemical group is attached to the third nucleic acid strand; (iv) providing, in the composition obtained in step (iii), conditions under which the chemical group and the compound or intermediate obtained in step (ii) will undergo reaction, thus providing a chemical compound or intermediate; wherein at least one of the steps (ii) or (iv) is performed in a solution predominantly consisting of an organic solvent.

It should be understood that, provided that the reaction of step (ii) is performed in a solution predominantly consisting of an organic solvent, the composition obtained in that step is transferred back into to an aqueous solution similar to the solution of step (i) before adding the third nucleic acid strand.

This method according to the invention is particularly flexible in respect of the order in which different reactions are to be performed. Thus, a method is provided for synthesizing products obtained by multiple reaction steps requiring different conditions, i.e. solvents. Furthermore, there is provided an easier method for synthesizing compounds requiring many reaction steps. For instance, it is not necessary to isolate the product of each reaction before continuing the next, thus saving time and increasing yields. Additionally, there is provided for the possibility that a specific reaction that will react both in an aqueous and an organic solvent can be performed more than once, thus increasing the product formation. Another advantage of the method is that the number of oligos to be used is rationalized.

By using the method of the invention is also made use of the possibility for providing compounds as a result of several reactions without compromising the ability to detect the history of each reactant. This is obtained by the fact that in a preferred embodiment a codon is present on each strand encoding the chemical group attached thereto. Thus, in the final composition according to a preferred embodiment where the oligos have been connected to each other, the compound obtained and all the codons encoding the starting chemical groups are attached to the same contiguous nucleic acid strand.

In another particular embodiment the third nucleic acid strand added in step (iii) forms a second and third stem thus resulting in a star structure having three stems. This is a preferred embodiment where the final product is obtained by the reaction of three different chemical groups. Thus, the final compound synthesized is present in a star structure defining three stems.

In yet another preferred embodiment, the method further comprises the steps of: (v) adding to the composition obtained in step (iv) a fourth nucleic acid strand forming a third and fourth stem of a star structure extending from a reaction center formed by nucleic acid duplexes, wherein a chemical group is attached to the fourth nucleic acid strand; (vi) providing, in the composition obtained in step (v), conditions under which the chemical group and the compound or intermediate obtained in step (iv) will undergo reaction thus providing a chemical compound; wherein at least one of the steps (ii), (iv) or (vi) is performed in a solution predominantly consisting of an organic solvent.

In this preferred embodiment the final composition is a four-stemmed star structure, wherein this particular star structure has the advantages as described previously. Namely that 4 stems will constitute a good balance between diversification of a subsequently formed library, the number of single stranded nucleic acids, the size of the compound obtained after reaction and the stability of the structure.

While the three and four-stemmed star structures are preferred embodiments, the same method can be continued so as to encompass 5, 6, 7, 8 and even more stems including the same number of additional reaction steps. This provides for synthesis of compounds requiring up to 8 and even more reaction steps.

In another preferred embodiment a loop is present at all extremes of the stems except one, so as to form a contiguous nucleic acid sequence. This contiguous nucleic acid sequence is very important for a subsequent extension and amplification reaction. This will furthermore in a particular embodiment provide a nucleic acid sequence where all the codons encoding each chemical group are present. In another embodiment an enzymatic extension reaction is performed in order to display the formed chemical compound.

BRIEF DESCRIPTION THE DRAWINGS

FIG. 3 shows a gel from an experiment reported in example 1.

FIG. 4 shows a gel from an experiment reported in example 2.

FIG. 5 shows a gel from an experiment reported in example 3.

FIG. 6 shows a gel from an experiment reported in example 4.

FIG. 7 shows a gel from an experiment reported in example 5.

FIG. 8 shows a gel from an experiment reported in example 6.

FIG. 9 shows a gel from an experiment reported in example 7.

FIG. 10 shows a gel from an experiment reported in example 8.

DETAILED DESCRIPTION OF THE INVENTION

Definitions

Figure 1:
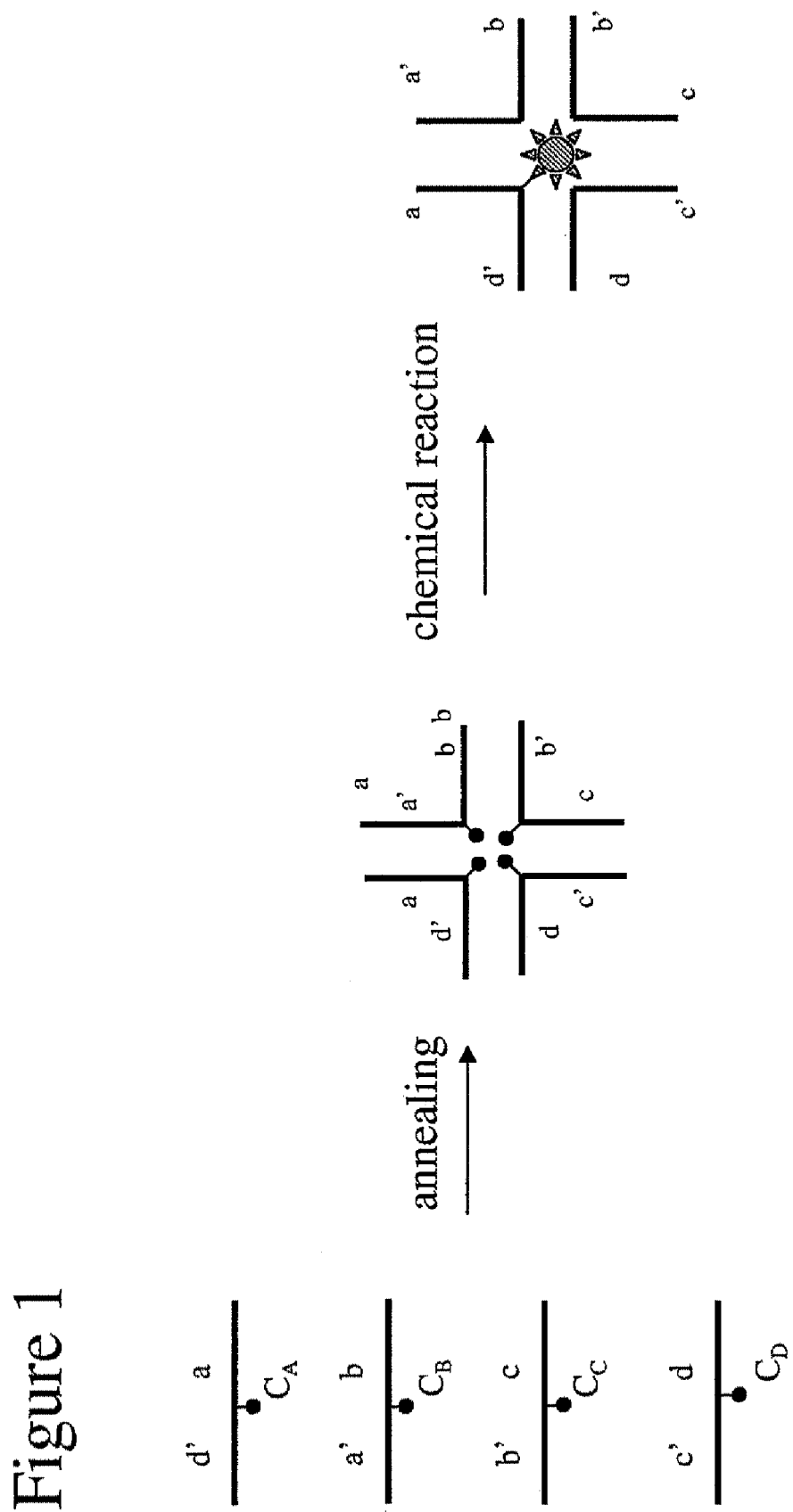
FIG. 1 depicts a reaction center and discloses steps in the formation in the star structure, in which the chemical groups are simultaneously reacted.

The term "aqueous solution" as used herein refers to a solution predominantly consisting of water, i.e. typically more than 50% (V/V) of the solution is water. An aqueous solution as used herein may comprise organic solvent. Functionally defined an aqueous solution is a solution in which the nucleic acids of the reaction are able to hybridize. Thus, in certain instances less than 50% (V/V) of water may be present, e.g. up to 60% (V/V) DMF may be present which is evident from the attached examples.

The term "star-structure" as used herein refers to any secondary structure involving at least three stems of mostly double stranded nature. 0, 1, 2, 3, 5, 6, 7, 8, 9 or more nucleotide residues may separate the stems. In the special case where zero nucleotide residues are separating four stems, the junction is called a Holliday junction. A star structure may consist of one contiguous nucleic acid molecule, or it may consist of a plurality of nucleic acid molecules.

The term "in or in the vicinity" as used herein refers to the position of the chemical groups in relation to the star structure. Thus, the nucleic acid duplexes, defining a star structure, surround a center or space in which a chemical reaction takes place. The chemical groups may be attached any where on the elements of the star structure provided that they will be able to meet the other chemical groups attached to other elements of the star structure for the purpose of effectuating a chemical reaction. Therefore, the chemical groups may be placed in the middle of the center, at the border of the center, outside the center but able to travel into the center by means of a linker etc.

The term "reaction center" as used herein defines that space mentioned above where the chemical groups are brought into proximity to each other by means of the star structure of the invention. As an example, FIG. 1 displays a 4-stemmed star structure defining a reaction center.

The term "organic solvent" as used herein refers to a chemical compound containing carbon to dissolve a solute.

The term "predominantly organic solution" as used herein has the opposite meaning than an aqueous solution. Thus, it is a solution in which nucleic acids of the invention are not able to hybridize due to the presence of organic matter. Typically, such a predominantly organic solution comprises more than 60% (V/V) of an organic solvent and preferably more than 70% (V/V) of an organic solvent. Such solutions may however in certain instances contain less organic solvent. For instance, more than 35% (V/V) acetonitrile or tetrahydrofurane (THF) are conditions under which the nucleic acids of the invention are not able to hybridize, which is evident from the attached examples, and can thus in the context of the present invention be seen as a predominantly organic solution.

As used herein the term "extendable joints" refers to an entity connecting the stems to each other and which entity can function as a template for a polymerase. Extendable joints may be naturally occurring nucleic acids or non-natural occurring nucleic acids modified at the base, phosphate and/or sugar moiety. Examples of non-naturally occurring nucleic acids are PNA (peptide nucleic acid) and LNA (locked nucleic acids) modified in the phosphate and sugar moieties, respectively. Usually, the chemical group participating in the reaction for preparing the compound is attached to a nucleotide in the joint.

As used herein two liquids are said to be "miscible" if they are partially or completely soluble in each other. When completely miscible there will be no visible phase separating the two liquids. The term "immiscible" has the opposite meaning. When immiscible or partially miscible a phase is visible separating the two liquids.

The term "reactant" as used herein refers to a compound or atom involved in a chemical reaction. Thus a reactant may without limitation be a starting material in a chemical reaction, a substance being converted in a chemical reaction, a substance participating in a chemical reaction without being consumed, such as a catalyst, etc. Preferably a reactant is any compound not associated with the reaction center of the star structure of the invention.

The term "large nucleic acid duplex" as used herein refers to duplexes formed of complementary nucleic acid strands of at least 50 bases. The duplex may be in the form of a star structure defining 3 or more stems each stem defining a duplex.

The term "attached" or "associated" as used herein describes the interaction between or among two or more groups, moieties, compounds, monomers etc, e.g. a chemical group and an extendable joint. When two or more entities are "attached" to one another as described herein, they are linked by a direct or indirect covalent or non-covalent interaction. Preferably, the attachment is covalent. The covalent attachment may be, for example, but without limitation, through an amide, ester, carbon-carbon, disulfide, carbamate, ether, thioether, urea, amine, or carbonate linkage. The covalent attachment may also include a linker moiety, for example, a photocleavable linker. Desirable non-covalent interactions include hydrogen bonding, van der Waals interactions, dipole-dipole interactions, pi stacking interactions, hydrophobic interactions, magnetic interactions, electrostatic interactions, etc. Also, two or more entities or agents may be "attached" to one another by being present together in the same composition. The terms attached and associated may be used interchangeably having the same meaning.

The term "linker" (or spacer) as used herein refers to an entity, which is long and flexible enough to allow the reactants to come into reaction proximity. The linkers preferably have a length and composition to permit reactions between reactants paired by oligonucleotides, but yet minimizing reactions with unpaired entities. The linker can be cleavable by for example light, oxidation, hydrolysis, exposure to acid, exposure to base, and/or reduction. The linker assists contact of the reactants and in certain embodiments, depending on the desired reaction, positions DNA as a leaving group, where the linker is cleaved as a natural consequence of the reaction.

Nucleic acid directed synthesis as described herein permits the production of combinatorial display libraries and the performance of selection and amplification of a broad variety of chemical compounds, in particular compounds obtained through water incompatible mechanisms. The nucleic acid serves multiple functions, for example, it brings chemical reactants together, guides the three-dimensional arrangement of chemical reactants, stores information regarding the chemical synthesis history, guides for proper matching of selected combinations of chemical reactants and allows diversification and breeding of chemical compounds.

The method may be used to assemble one molecule, trillions of molecules, or even more at a time.

The method allows the isolation of ligands or drugs with properties superior to those isolated by traditional rational design and combinatorial drug discovery methods, as the chemical space can be systematically searched for ligands having desired properties.

Nucleic acid directed synthesis has been shown to be a wide-ranging phenomenon, not only limited to compounds of nucleic acid nature, but also applicable to guiding a broad range of chemical reactions under a broad range of conditions (WO 2004/016767, WO 2002/074929A2). This is of particular importance, as most molecules of interest do not resemble nucleic acid or nucleic acid analogs. The chemical groups participating in the formation of the final chemical compound may be transferred in one step to a receiving chemical entity on a scaffold or a chemical group may be transferred in two steps, in which the first step includes a cross link between the chemical group and the receiving entity and the second step include a cleavage of the chemical group from the carrier module to complete the transfer. An example of the former type of reaction is a carrier module having attached a 5-membered substituted N-hydroxysuccinimid (NHS) ring serving as an activator, i.e. a labile bond is formed between the oxygen atom connected to the NHS ring and the chemical group to be transferred, this approach is for example useful for amine acylation reactions as described in details below. The chemical groups can be transferred to a recipient nucleophilic group, typically an amine group, which may be present on a scaffold. The remainder of the fragment is converted into a leaving group of the reaction. When the chemical group is connected to the activator through a carbonyl group and the recipient group is an amine, the bond formed on the scaffold will be an amide bond.

Of pivotal importance for nucleic acid directed synthesis of combinatorial display libraries is the proximity guiding of reactants, which ensures reaction efficiency and proper association of encoding and display. Proximity of reactants is obtained by associating together the reactants, by some sort of linker. Proximity can also be described as a local concentration, which is dependent on the length and flexibility of the linker. If free flexibility of the linker is assumed, the local concentration can be calculated by using the volume of a sphere with the linker length as radius. The formula to calculate the volume of a sphere is; $v=4/3*pi*r^3$. Consequently, the proximity or local concentration drops in the $3^{rd}$ power as a function of the linker length. For example a linker length around 10 nm will be equivalent to a concentration around 1 millimolar, whereas a 100 nm linker will be equivalent to a concentration around 1 micromolar. Efficient organic chemistries are typically performed in the millimolar to molar concentration range. Consequently, to ensure efficiency in the chemical reactions the linker length should not be significantly longer than 10 nm.

Preferably, the reactive groups are brought into reactive proximity of less than 100 nm, more preferably less than 50 nm, even more preferably less than 25 nm, even more preferably less than 10 nm and most preferably less than 5 nm.

In the prior art for single-pot synthesis of DNA encoded display libraries allowing amplification, single stranded DNA templates with codons spread out over the length of template are used (WO 2004/016767, WO 2002/074929A2). The templates are responsible for recruiting transfer units having proper anti-codon sequences from a repertoire of transfer units and thereby bringing together chemical groups on the template and the transfer unit. Consequently, the single stranded template acts also as a linker between the chemical group on the template and the chemical group on the transfer unit hybridized to the template. Hence, the linker length and thereby the local concentration of reactants will depend on which codon position is employed. An unfolded (extended) oligonucleotide having for example 20 nucleosides will have a length around 10 nm, (the six-bond backbone spacing is around 0.63 nm) and an oligonucleotide having 200 nucleosides will have a length around 100 nm. Consequently, unfolded oligonucleotides considerably longer than 20 nucleosides (10 nm, equivalent to a concentration around 1 millimolar) will in general not be suitable to create proximity guiding of chemical reactions.

Nucleic Acid Composition

In the present invention the lengthened structure of nucleic acid in use to bring reactants into reaction proximity is circumvent. This is achieved by choosing appropriate sequences of oligonucleotides capable of folding into stable three dimensional structures, thereby allowing proximity guiding by sequence positions separated by many nucleosides. As shown in FIG. 1 this is achieved by using bi-specific oligonucleotides (mutually complementary), which can hybridize into a "starstructure". The bi-specific oligonucleotides contain two segments: a segment towards the 3' end of one oligonucleotide hybridizes to a segment towards the 5' in the next and so forth. Finally, the segment towards the 3' end of the last hybridizes to a segment towards the 5' end of the first oligonucleotide. Consequently, the mid section between the two segments on each oligonucleotide is pointing towards the center. This mid section can be a bond or a segment. In contrast, the termini are pointing outwards, thus giving the star-structure. So, when three types of oligonucleotides are used three stems are formed, when four types of oligonucleotides are used four stems are formed etc. A chemical group is conveniently attached to or is in the vicinity of the mid section on each oligonucleotide. The chemical groups are thus brought into reaction proximity, as the diameter of the DNA double helix is around 2 nm, thus allowing proximity directed chemical reactions to occur in or in the vicinity of the center, called the reaction center.

The reaction center is defined by the stems surrounding said center. It has been suggested, that the distance between two reactants in the reaction center is less than 10 nm. Assuming the reaction center is spherical; the concentration of the reactants can be calculated to 1 mM. In a biological context a concentration of this size is regarded as high and a reaction can be assumed to proceed within a reasonable time. Furthermore, the concentration of free reactant in the media is very low, when the carrier modules have been dosed in adjusted molar amounts, so the reaction in the reaction center is greatly favored over non-directed reaction.

When the chemical group is attached to the backbone the point of attachment is generally at the phosphor of the internucleoside linkage. When the nucleobase is used for attachment of the chemical group, the attachment point is usually at the 7th position of the purines or 7-deaza-purins or at the 5th position of pyrimidines. The nucleotide may be distanced from the reactive group of the chemical group by a spacer moiety. The spacer may be designed such that the conformational space sampled by the reactive group is optimized for a reaction with the reactive group of another chemical group in the reaction center. In general, the chemical group is associated to the midsection through one or more covalent bonds.

The reactants may originate from any source, including being a compound added to the media as a free reactant not associated with a nucleic acid. The further reactant(s) may be scaffolds, cross-linking agents, activating agent, deprotecting agents etc.

The chemical reaction is performed such that the formed product eventually is attached to at least one oligonucleotide. Furthermore, a codon is conveniently situated external to one or both of the hybridized segments on each oligonucleotide, thus allowing encoding of the chemical groups. The oligonucleotides with an attached chemical group, two position specific hybridization segments and optionally a codon are in the following called carrier modules for convenience.

To make the created combination of oligonucleotides amplifiable by e.g PCR, the termini in each stem, except one, are in an embodiment ligated via loop formations to form a continuous oligonucleotide with a 5' and 3' termini. In one aspect, the structure consists of one stem and a number of stem-loops, which can be amplified by having PCR priming sites at the termini. Alternatively, all termini are ligated forming a closed ring, which may be amplified by primer extension by a DNA polymerase without strand displacement activity.

Oligonucleotides are used to direct the chemical reactions in the present invention. The oligonucleotides in this context are called carrier modules, which contain at least two position specific hybridization oligonucleotide segments, optionally an oligonucleotide codon segment, and a chemical group.

In one embodiment the present invention relates to carrier modules, where the oligonucleotide portion consists of DNA, RNA or analogs hereof and in any combinations hereof. The oligonucleotide portion is capable, at least after modification, of being an appropriate template in standard protocols for nucleic acid replication and/or amplifications.

The carrier modules may be synthesized using methodologies known in the art. For example the oligonucleotide may be prepared by any method known in the art for synthesizing oligonucleotides, e.g. solid phase synthesis using an automated synthesizer. Oligonucleotides following synthesis may be associated when desired (for example, covalently or non-covalently coupled) with a chemical group of interest using standard coupling chemistries known in the art.

In one embodiment the present invention relates to carrier modules, where the association of the chemical group to the oligonucleotide is to the mid section between the hybridization segments or in the vicinity hereof. The mid section may be a phosphordiester linkage, derivatives thereof or a nucleic acid segment. In vicinity of the mid section relates to locations on the duplex nucleic acid stem, preferentially to locations close to the mid section. Preferably, the vicinity of the mid section relates to less than 20 nucleotides, more preferably less than 10 nucleotides, even more preferably less than 5 nucleotides and most preferably less than 2 nucleotides.

In one embodiment the present invention relates to carrier modules, where an association of a chemical group to an oligonucleotide occurs via linkers or spacers, which are long and flexible enough to allow the reactants to come into reaction proximity. The linkers preferably have a length and composition to permit reactions between reactants paired by oligonucleotides, but yet minimizing reactions with unpaired entities. Moreover, the association between the oligonucleotide and the chemical group may be through a covalent bond. In certain embodiments, the covalent bond may be more than one.

The linkage can be cleavable by for example light, oxidation, hydrolysis, exposure to acid, exposure to base, or reduction. A variety of linkages useful in the practice of the invention are described in the prior art (Fruchtel and lung, Angew Chem Int Ed Engl, 35, 17, 1996). The linker assists contact of the reactants and in certain embodiments, depending on the desired reaction, positions DNA as a leaving group, where the linker is cleaved as a natural consequence of the reaction. In certain embodiments depending on the desired circumstances reaction of one reactive group is followed by cleavage of the linker attached to a second reactive group to yield products without leaving behind additional atoms capable of providing chemical functionality. When choosing linker and cleaving conditions it is advantageous to have one linker that cleaves under different conditions than the others. In this way there is provided for selective cleavage of linkers ultimately resulting in the chemical compound attached to the reaction center only by means of one linker.

If the chemical group is of a certain length it may not be necessary to add a linker or spacer in order to facilitate the proximity guiding. If for instance at least one of the groups is a long carbohydrate chain having a reactive group in one extreme, the chemical group itself will fulfil the function of a linker.

In one embodiment the present invention relates to carrier modules, where the association of the chemical group to the oligonucleotide occurs through the backbone of the nucleic acid.

In one embodiment the present invention relates to carrier modules, where the association of the chemical group to the oligonucleotide is through the base. In an embodiment the chemical group is associated to the non-Watson-Crick hydrogen bonding parts.

In one embodiment the present invention relates to carrier modules, where the association of the chemical group to the oligonucleotide allows read through by a DNA polymerase, at least after its removal.

In one embodiment the present invention relates to carrier modules, where the association of the chemical group to the oligonucleotide is non-covalent. For example if biotin is attached to the oligonucleotide and streptavidin is attached to the chemical group, hence an interaction between biotin and streptavidin associates the oligonucleotide and the chemical group with each other non-covalently.

The Method of the Invention

In the method of the invention the composition described in various aspects above is prepared in an aqueous solution. Such a solution is one that facilitates hybridization of the carrier molecules into the star structure of the invention. For the structures of the present invention, such an aqueous solution will typically comprise a sodium salt, such as NaCl, in a concentration in the mM range, for example 50-200 mM NaCl. It is well known to the skilled person that the higher the Tm of the duplex the higher NaCl concentrations may be applied. However, in the context of the present invention low concentrations are desirable. For the subsequent step ii) of the method, the presence of substances from the aqueous solution, besides the composition, should preferably be minimized. The chemical groups or reactants include a variety of reagents and can be any chemical agent or reactive moiety (e.g. electrophiles, nucleophiles) known in the chemical art.

Transferal of the composition obtained in the aqueous solution to a solution predominantly consisting of an organic solvent may be performed in any suitable way. The aqueous solution may in a preferred embodiment simply be diluted with organic solvent; alternatively a sample of the aqueous solution comprising the composition may be added to an organic solvent. Several other ways of buffer exchange exist such as precipitation or concentration and subsequent dissolution in the organic solvent, buffer exchange using a column. Yet other means are lyophilization, concentration, dialysis etc. These are all techniques that are well known in the art.

Depending on the transferal of the composition obtained in step (i) there will typically be minute amounts of water and a sodium salt present in the predominantly organic solution of step (ii). Importantly, according to the method it is not necessary to add any stabilizing compounds for the nucleic acid duplexes constituting the inventive star structure, they will remain stably hybridized when transferred to the organic solution. This finding was initially explored by Rozenman and Liu (see above). However, in an embodiment it may be necessary to add an agent or solubilizer, which can aid the dissolution of the composition in case the water content is substantially zero. For example, said agent may become relevant in embodiments where the composition is precipitated or concentrated and is to be dissolved in the organic solvent.

The organic solvent may be any suitable solvent for a particular reaction to be performed. The organic solvent may also comprise mixtures of organic solvents. Both water miscible and immiscible solvents; protic and aprotic solvents etc. are contemplated. The proximity guiding provided by the star structure secures a high rate of reaction between the chemical groups. Still, the choice of solvent depends on the chemical groups/reactants, especially when reactants not associated with the reaction center are used, because the rate of reaction of these reactants depends on their salvation in the solvent. As a general rule the rate of reaction decreases with an increasing degree of solvation. The choice of solvent is within the skill of the art. Solvents may be but are not limited to acetonitrile, THF, DMF, pyrrolidine, dichloromethane, dioxane, N-methylpyrrolidinone (NMP), dimethylacetamide (DMA), formamide, nitromethane, methanol, ethanol, propanol, tert-butanol, dimethylsulfoxide (DMSO), ethylene glycol, acetone, 2,2,2-trifluoroethanol (TFE), hexafluoro-2-propanol, sulfolane, 2-propanol, 1-butanol, 2-butanol, tetrahydropyran, nitroethane, 2-butanone, 2-methoxyethanol, ethylene glycol dimethyl ether chloroform, 1,2-dichloroethane, tetrachloromethane, toluene, benzene, ethyl acetate, propionitrile, diethylether, methyl tert-butyl ether (MTBE), alkanes (e.g. pentane, hexane, heptane) and combinations thereof.

The ratio of organic solvent to water in the solution obtained in step (ii) of the method highly depends on the reaction. Some reactions involve reactants, not associated with the reaction center, that are incompatible with water either because they are insoluble which means that they will not be able to "meet" the chemical groups in the reaction center or because they decompose, hydrolyze or become inhibited by the presence of water. As the solution obtained in step (ii) predominantly consists of an organic solvent the content thereof is generally higher than 60% (V/V), preferably higher than 70% (V/V), e.g. 70-99.9; 70-99; 70-95, 90-99, 90-95, 90-99, 95-99 or 95-99.9 and even ~100% (V/V). However, since the term "predominantly consisting of an organic solvent" as mentioned above also should be understood functionally, namely as an organic solvent in which single stranded nucleic acid strands would not be able to hybridize, the content of organic solvent may in certain instances be lower than 50% (V/V), this is exemplified in the attached examples.

When transferred to the predominantly organic solvent, the solution obtained is provided conditions under which reaction between the at least two chemical groups will proceed. The specific conditions depend on the nature of the reaction to be performed. Thus, additional reagents not associated with the reaction center may be added, such as but not limited to catalysts, protecting groups, acids, bases etc., the temperature, pressure, pH etc. may be adjusted, light may be applied aerobic/anaerobic conditions may be applied etc. These are all examples of parameters, which may be provided to the solution predominantly consisting of an organic solvent or an aqueous solution according to an embodiment in order to bring a about a desired reaction. The exact choice of conditions is within the skill of the art.

In order to elucidate more on the types of parameters/conditions, which are provided to the solution a number of reactions, which may be performed according to the invention, are exemplified below.

Thus, the types of reactions to be performed are for example and preferably Wittig and related reactions, Aldol condensations, Heck reactions, reductive amination, amine acylation, alkyne-alkene oxidative coupling, Michael addition and Sonogashira coupling, all reactions are in this context to be understood as generally understood in the art of organic synthesis.

Thus, a Wittig and related reaction refers to alkylidene-deoxo-bisubstitutions where an aldehyde or ketone is treated with a phosphorous ylide/phosphorane to give an olefin. In the context of the present invention, the phosphorous ylide and the aldehyde/ketone are attached in or in the vicinity of the reaction center as the chemical groups.

The reaction is illustrated below:

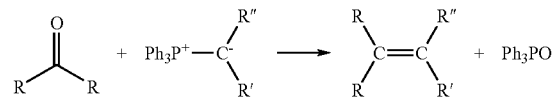

wherein Ph is a phenyl group. R is H, an aliphatic, alicyclic and/or aromatic group; the group may contain double or triple bonds; it may contain various functional groups such as OH, OR, $NR_2$, aromatic nitro or halo, acetal, or ester groups though resulting in a lower yield due to the subreaction between the ester group and the phosphorous ylide. It should be noted that one of the groups, R, is attached in or in the vicinity of the reaction center.

The functional groups (R' and R") of the phosphorous ylide may also contain double and triple bonds and certain functional groups. Simple ylides (wherein R, R' are hydrogen or alkyl) are as known in the art very reactive and require conditions where oxygen, water, hydrohalic acids, alcohols, carbonyl compounds and carboxylic ester are absent, besides the group intended for reaction, namely the aldehyde or ketone (March, *Advanced Organic Chemistry* $4^{th}$ ed. p. 956 ff.). Those functional groups mentioned above that are present on the nucleic acid strands should not be substantially affected since the hybridization of the strands into the star structure forces the chemical groups to react with each other alone, and the nucleic acid strand may confer a stabilizing effect to the ylide. However, when such simple phosphorous ylides are employed water should preferably be absent form the solution.

More preferred are phosphorous ylides having an electron withdrawing group such as COR, CN, COOR, e.g. $COCH_2$, in the α-position because these ylides are much more stable. These ylides, however, react slowly or not at all with ketones. A slow reaction normally encountered in Wittig reactions using these ylides may in the present invention be speeded up because the reactants are forced together by the proximity guiding provided by the star structure. Still other functional groups allowed on the phosphorous ylides may comprise a halogen, an α-OR or -OAr group. The Wittig reaction comprises several additional variations and related reactions, which are useful for controlled localization of double bonds. The skilled person will know how to vary the conditions of the Wittig and related reactions in order to obtain a desired product.

Wittig reactions may, using the nucleic acid directed synthesis of the invention, take place both in an aqueous and an organic solvent under basic conditions, such as NaOH or pyrrolidine. Preferably, the reaction takes place in a water miscible solvent such as acetonitrile. The reaction may take place, though with a lower yield, without the addition of a base, the base e.g. being NaOH. The reaction suitably takes place at room temperature.

Aldol condensation is another example of reactions to be performed according to the invention.

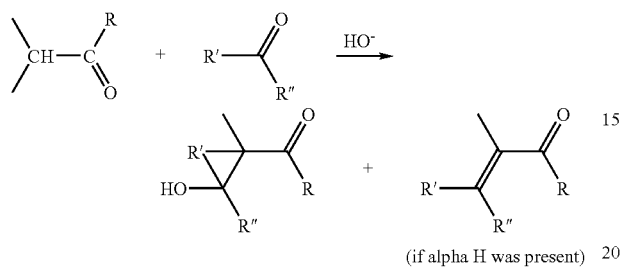

(if alpha H was present)

In the aldol condensation/reaction the α-carbon of one aldehyde or ketone adds to the carbonyl carbon of another to give a β-hydroxy aldehyde or ketone and in certain variations of the aldol reaction an ester or imine is used. The aldol reaction is often followed by dehydration. Normally the aldol reaction is performed under basic conditions, such as with OH⁻, pyrrolidine, stronger bases, such as aluminum t-butoxide, and in certain variations (where an imine is used) LiN(iso-Pr)$_2$. The nature of the aldehydes/ketones may vary, for example an aldehyde, such as benzaldehyde, may be reacted with a ketone, such as methyl-propyl ketone. For the purpose of the present invention one of the groups at the opposite extremity of the functional group intended of the reaction is attached in or in the vicinity of the reaction center.

Aldol reactions are also a suitable means for preparing five- and six membered rings, a variation of this type is called the Robinson Annulation, a combined Michael addition and aldol condensation, a reaction often used to prepare steroids and terpenes.

According to the invention, the aldol condensation may be performed both in an aqueous solution and a solution predominantly consisting of an organic solvent (95% Acetonitrile is exemplified) at room temperature however giving a higher yield in the organic solution.

Heck Coupling

The Heck coupling/reaction is an arylation of olefins by treatment with "aryl palladium". The "aryl palladium compound" is obtained by treatment of an arylhalide, such as aryliodide or -bromide, with a palladium complex, such with triarylphosphine, (dba)$_3$.CHCl$_3$ or tris(4,6-dimtehyl-3-sulfanatophenyl)phosphine trisodium salt hydrate (TXPTS).

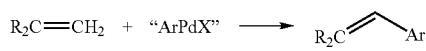

Wherein AR is an aryl group, wherein the aryl group carries a functional group capable of binding in or in the vicinity of the reaction center. The nature of the groups "R" is not restricted except that at least one of the groups should be able to bind in or in the vicinity if the reaction center. Thus, R may simply be an unsubstituted olefin such as pentene (only having a functional group in the other extreme than the double bond for binding to the reaction center). The alkene may also be substituted e.g. with ester, ether, carboxyl, phenolic, or cyano groups. Even though increased substitution normally decreases reactivity this has minor importance in the present invention, as the proximity guiding has already increased the reaction rate.

The Heck reaction may suitably take place both in an aqueous solution and a solution predominantly consisting of an organic solvent such as acetonitrile and THF. The reaction takes place at room temperature.

Another reaction is alkyne-alkene oxidative coupling resulting in α,β-unsaturated ketones. Such α,β-unsaturated ketones may be used for further synthesis e.g. in the 1,4-addition and are thus also building blocks in organic synthesis.

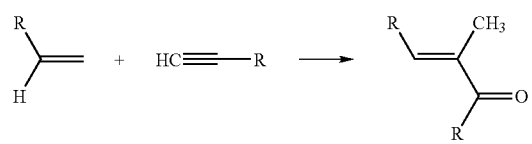

Wherein each of the groups R may be substantially any group that at the other extreme will bind to the reaction center. Preferred R groups are straight-chained carbohydrates bearing e.g. a carboxylic at the extreme opposite the double/triple bond for formation of an amide bond with the nucleic acid of the reaction center, such as petenoic acid and heptynoic acid.

The reaction is Pd catalyzed, e.g. it may be performed using Na$_2$PdCl$_4$ alone or in combination with TXPTS. The reaction may using the composition of the invention, be performed in both aqueous and organic solvent, such as acetonitrile.

Another preferred reaction is the Sonogashira coupling wherein a terminal alkyne is reacted with an aryl or vinyl halide.

Thus, in an aspect of the invention is provided a method for Preparing an aqueous solution comprising a composition forming a star structure defining 3 or more stems extending from a reaction center, each stem being formed by a nucleic acid duplex, and at least 2 chemical groups being attached in or in the vicinity of the reaction center and providing, in the solution obtained, conditions under which the at least 2 chemical groups will undergo a Sonogashira Coupling thus providing a chemical compound where a substituents has been added to a terminal alkyne.

There are no particular restrictions on the substituents on the terminal alkyne and the aryl or vinyl halide i.e. the terminal alkyne may be an unbranched alkyne, such as heptyne, and the halide may be an aromatic compound such as a phenyl compound attached in or in the vicinity of the reaction center.

Basically, the reaction requires two catalysts, typically a zero valent Pd complex, examples are Na$_2$PdCl$_4$, Pd(PPh$_3$)$_2$Cl$_2$, Pd(OAC)$_2$/DABCO, Pd(PPh$_3$)$_4$ or Pd/C, and a salt of copper(I), for example CuSO$_4$ or CuI, but variations have been reported.

Figure 2:
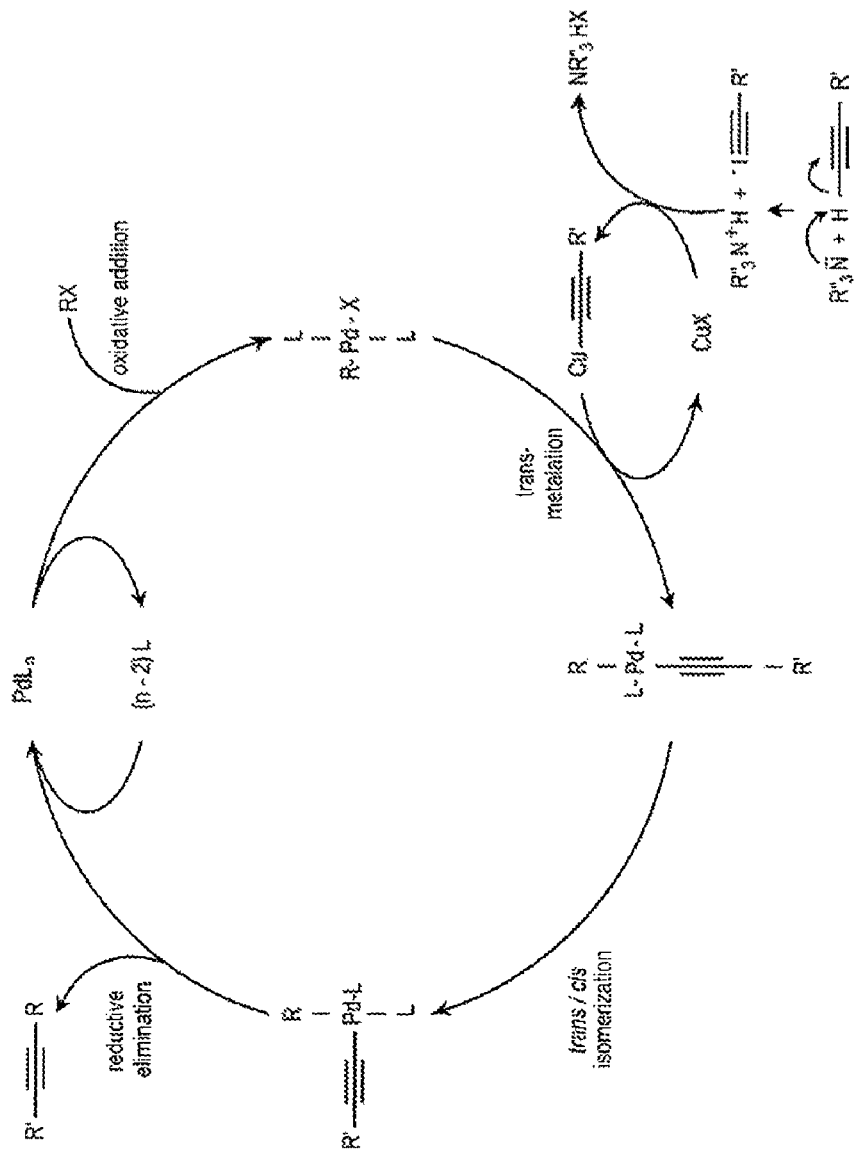
FIG. 2 is a reaction scheme outlining the general principles of the Sonogashira coupling.

The mechanism in one variation proceeds through the following mechanism as illustrated in scheme I of FIG. 2 where, as indicated above, R and R' may be any group desired in the final product provided with a functional group for attachment to the reaction center.

The palladium complex activates the aryl halides (vinyl halides may be used similarly) by oxidative addition thereof into the carbonhalogen bond. The copper(I) halide reacts with the terminal alkyne to produce a Cu-acetylide thus producing an activated species.

The activated Cu-acetylide and the palladium complex added organic halide reacts through a transmetalation reaction producing an arylated alkyne interspaced by the palladium-ligand complex. Final isomerization and reductive amination yield the product.

The conditions under which the reaction proceeds are typically anhydrous and anaerobic. However, recent development of palladium catalysts which are oxygen stable have reduced the need for anaerobic conditions. Moreover the reaction medium should preferably be basic when a Copper halide is used in order to neutralize the hydrogen halide byproduct. Typically an alkylamine compound, such as triethylamine and diethylamine, is used as solvent.

Furthermore it has been shown that when performing the reaction using the star structure of the invention the reaction may take place both in an aqueous solution and a solution predominantly consisting of an organic solution depending on the nature of the compounds and the catalysts or other conditions to be used.

For instance when using a Cu(I) co-catalyst it is believed, without the wish to bound by any theory, that DNA is damaged by Cu(I) in an aqueous solution resulting in a lower product yield and thus favoring reaction in a solution predominantly consisting of an organic solvent. However, recent developments of the reaction (see below) omit the use of a Cu co-catalyst and this variation of the reaction may be particular suitable if the reaction is to be performed in an aqueous solution.

Copper free mechanisms have, as briefly mentioned above, been reported using a strong base or an amine as a solvent (Alani et al. *Tetrahedron Lett.* 1995, 34, 6403). The advantage of omitting copper is avoiding, as a byproduct, the formation of diynes.

Also mechanisms omitting palladium metal, ligand and copper have been reported (Borah et al., *SYNLETT* 2005, 18, 2823-25). Instead of the Pd/Cu catalyst system InCl$_3$ in dry benzene is added under reflux (80° C.). This mechanism has the advantage that expensive palladium complexes are omitted and the reaction is simpler requiring fewer reactants. The drawback of this mechanism is the heating to 80° C., which may denature DNA duplexes used in traditional DNA templated syntheses if their Tm is exceeded. However, the star structure of the invention, being more stable than duplexes of e.g. 20 bases due to a higher degree of hybridization, may be suitable for this reaction.

As exemplified above various methods exist for performing the Sonogashira coupling in respect of conditions such as catalyst, solvent, temperature, reaction time, etc. The present invention should not be restricted to any particular variant of the reaction and it is within the skill of the art to choose appropriate conditions for a particular reaction.

Yet another reaction according to the invention is reductive amination as outlined below.

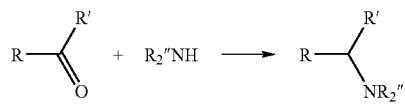

Reductive amination is, as can be seen form the above, a reaction in which an aldehyde or ketone is treated with ammonia or a primary or secondary amine under reductive conditions in order to prepare an amine of a higher order, i.e. if a primary amine was the chemical group, the product will be a secondary amine and so forth. The groups R, R' and R" may be H or a suitable substituents. Again, one of the groups must bear a functional group capable of binding to the nucleic acid of the reaction center. An example of the R groups may be benzaldehyde functionalized with a carboxylic acid group for binding to the nucleic acid and a simple NH$_2$-group from the nucleic acid of the reaction center. The conditions under which the reaction is performed may be in the presence of hydrogen and a catalyst, such as Ni, or using e.g. Zn and HCL or sodium cyanoborhydride as the reducing agent(s). As is well known in the art there exist several more reducing agents. The reaction may using the composition of the invention be performed both in an aqueous and organic solvent, such as DMF.

Another reaction according to the invention is the Michael Addition or reaction, wherein compounds containing electron-withdrawing groups are, in the presence of a base, added to olefins similarly containing an electron-withdrawing group.

The general reaction scheme can be seen below:

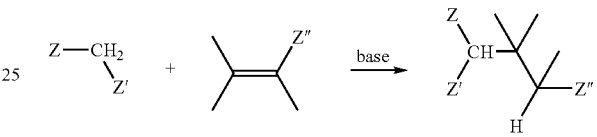

As mentioned above the group "Z" should be an electron-withdrawing group. The first listed compound is the "Michael donor" and the compound bearing the double bond is the "Michael acceptor". The Donor is normally an active methylene, however, according to the invention the donor may be a nucleophile, such as a thiol or amine group, attached to the nucleic acid. The acceptors are activated olefins such as α,β-unsaturated carbonyl compounds, for example maleimide or cinnamide, bound to the nucleic acid of the reaction center at the end opposite to the ring structure. The first step of the reaction is the formation of an anion in the "Michael donor". This anion is formed by the base and facilitated by the electron-withdrawing group; this may be any electron-withdrawing group known in the art. Alternatively according to the invention the Michael donor is a nucleophile and in such cases no acidic proton is removed. The next step is a nucleophilic attack, by the anion formed/the nucleophile, at the electrophilic alkene, the "Michael acceptor", followed by an acid-base reaction resulting in the final 1,4-added product. The alkene may be any suitable one, but is preferably a cyclic compound, such as maleimide or cinnamide. The Michael system has a large range of applications such as in the Robinson annulation as previously mentioned.

The Michael addition may be performed both in an aqueous and organic solvent. However, depending in the donor and acceptor reactions may be favored in an organic solvent, e.g. when the donor is a thiol and the acceptor is cinnamide.

Finally should be mentioned amine acylation, a formation of an amide bond like the peptide bond from a carboxylic acid and an amine, this reaction may also be performed using the method according to the invention.

Variations of the method are contemplated such as the insertion of a reaction step (ia) between step (i) and (ii). As it is well known in the art that a specific reaction may proceed through a multiple step series it is convenient to be able to change the reaction environment. In this variant of the method, the at least three stemmed composition bearing at least 2 chemical groups is reacted first in an aqueous solution and subsequently in a solution predominantly consisting of an organic solvent.

As mentioned above the stems may be unconnected but are preferably connected in particular by a joint, which is extendable by an enzyme, depending on the nature of moieties of the extendable joints the enzyme may be a polymerase when the moiety is a nucleic acid or an analogous thereof. Since the compounds obtained in the method of the invention ultimately are to be used in a library it is very convenient that the stems of the star structure are interconnected both in the reaction center and in the extremes. Such a contiguous nucleic acid bearing the obtained product can easily be extended, amplified and/or displayed by methods known in the art.

Carrier Modules

A broad range of compounds and/or libraries of compounds can be prepared using the method described herein as elucidated above. In one embodiment the present invention relates to sequential chemical reactions of proximity guided reactants, for example, by use of orthogonal chemistries or the use of orthogonal protective/masking groups, or by sequential assembly and reaction of carrier molecules.

The assembly of carrier modules without ring formation, i.e. formation of a contiguous nucleic acid, may by itself bring appropriately located chemical groups into proximity, as the diameter of a double helix is around 2 nm thus allowing positioning of several consecutive chemical groups within reaction proximity. The reaction conditions, linkers, reactants and reaction site are chosen to avoid non-oligonucleotide guided reactions and accelerate oligonucleotide-guided reactions. Sequentially or simultaneously contacting of carrier molecules can be employed depending on the particular compound to be synthesized. In a certain embodiment of special interest, the multi-step synthesis of chemical compounds is contemplated in which three or more carrier molecules are contacted sequentially to facilitate multi-step synthesis of complex chemical compounds.

In one embodiment the present invention relates to annealing of carrier modules, which allows the use of carrier modules at concentrations lower than concentrations used in many traditional organic synthesis. Thus, carrier modules may be used in submillimolar concentrations. Preferably, the carrier module concentrations may be used in submillimolar concentrations of less than 100 micromolar, more preferably less than 10 micromolar, even more preferably less than 1 mlcromolar, even more preferably less than 100 nanomolar and most preferably less than 10 nanomolar.

The present invention is based on the realization that the hybridized super structure remains assembled even at conditions in which a hybridization between the individual nucleic strands would not proceed. Further methods for fixation of the star structure are contemplated. According to a certain method for preparing an encoded molecule, the method comprises the initial step of preparing an aqueous solution comprising a composition forming a star structure defining 3 or more stems extending from a reaction center, each stem being formed by a nucleic acid duplex and at least 2 chemical groups being attached in or in the vicinity of the reaction center. Subsequently, the star structure is fixed, i.e. the nucleic acid strands are hampered in dehybridizing. As a last step, conditions are provided under which the at least 2 chemical groups undergo reaction, thus providing a chemical compound.

The preservation of the structure by fixation may be conducted in a variety of ways. In a certain aspect, the fixation is provided by a polymer. Suitably, the polymer chains have the ability to encapsulate or in another way inhibit the movement or de-hybridization of the individual nucleic acid stands of the star structure. The polymer may preferably be soluble in the aqueous solution in which the star structure initially is provided.

Preferred polymers include DEAE Sepharose, DEAE dextran, agarose and polyacrylamide. DEAE Sepharose and agarose is commercially available, while polyacrylamide can be prepared in situ. In a specific embodiment, the polyacrylamide is produced in situ by adding to the aqueous solution comprising the star structure acrylamide/bis-acrylamide, tetramethylenediamine, and ammonium persulphate. Alternatively, a melt of a polymer like polyacrylamide or agarose is prepared and the star structure is molded into polymer. In a certain embodiment, the star structure is initially run in a gel, such an agarose gel or a polycrylamide and subsequently the piece of gel comprising the star structure is cut out and used in the reaction step. The latter method has the advantage that impurities and unreacted reactants are removed.

A way of fixating or "imprinting" the star structure includes precipitation. As examples, the star structure can be precipitated on a surface, such as gold or glass, on a filter or similar pervious means. Precipitation may be effected by means well known to the skilled person and includes lyophilisation, salination, addition of incompatible solvents etc. Also, affinity bounding of the star structure is a possible way of obtaining an imprinting. Apart from the DEAE sepharose and dextran mentioned above, affinity bonding may be effected by silica or hydroxyapatit. In another embodiment the imprinting is performed by binding the star structure to a surface, such as a bead or a similar body with a hard surface. In another embodiment, the star structure is absorbed in a membrane and preserved in the membrane pores. In yet another embodiment, crystals are prepared of the star structure.

After the imprinting step follows the reaction step. Dependent on the specific nature of the chemical groups to be reacted and the chemical reaction to proceed, the conditions may be selected within a wide range of temperature, solvent, concentration of reactant/coreactant, etc. In an aspect, the temperature of the reaction is selected above the melting temperature of the star structure in aqueous solution.

Preparation of Combinatorial Library

An important practical difference between traditional and nucleic acid directed library synthesis is the scale of each manipulation. Due to the amounts of material needed for screening and compound identification, traditional combinatorial syntheses typically proceed on nanomol-micromol scale per library member. In contrast, nucleic acid directed library synthesis can take place on the femptomol-picomol scale because only minute quantities (e.g. about 10-20 mol) of each nucleic acid-linked synthetic molecule are needed for selection and PCR amplification. The vast difference in scale, combined with the single-solution format in nucleic acid directed library synthesis simplifies significantly the preparation of materials required.

In one embodiment, the present invention relates to the formation of a combinatorial display library. Libraries can be produced by use of repertoires of carrier modules on some or on all positions. In a first step a repertoire of carrier modules for each position is provided. When the carrier modules are mixed under hybridization conditions, they will assemble into the star structure, directed by the sequence of the hybridization segments. After assembling the carrier modules ligation and reaction is effected in any order. In an aspect of the invention, the ligation is performed before the reaction to increase the stability of the star structure. Subsequent to the proximity guided reaction, a polymerase priming site is ligated to the star structure and an extension reaction is preformed to display the formed chemical compound to the exterior environment.

As would be appreciated by one skilled in this art, libraries of small molecules and polymers can be synthesized using the principles disclosed herein. Consequently, the combinatorial display library can be subjected to selection and the enriched library's members identified through their encoding oligonucleotide.

Depending upon the circumstances repertoires of carrier modules for two or more positions are initially combined and subjected to a nucleic acid guided chemical reactions between the attached chemical groups. Depending upon the circumstances the library can be formed by multiple chemical reactions, wherein each intermediate product is purified before the subsequent round of reactions. Preferably less than 20 chemical reaction steps are required to create a library. In other embodiments, less than 10 chemical reaction steps are needed, and more preferably between 3 and 9 steps are needed to create a library Selection Selection and/or screening for reaction products with desired activities (such as catalytic activity, binding affinity, binding specificity or a particular effect in an activity assay) might be performed according to any standard protocol. For example, affinity selections may be performed according to the principles in library-based methods such as phage display (Smith, Science, 228, 1315-7, 1985), ribosome display (Hanes et al., Proc Natl Acad Sci USA, 95, 14130-5, 1998), mRNA display (Roberts and Szostak, Proc Natl Acad Sci USA, 94, 12297-302, 1997) or DNA encoded chemical libraries (WO 2004/016767, WO 2002/074929A2). Selection for catalytic activities may for example be performed by affinity selection on transition state analog affinity columns (Baca et al., Proc Natl Acad Sci USA, 94, 10063-8, 1997) or by function based selection schemes (Pedersen et al., Proc Natl Acad Sci U S A, 95, 10523-8, 1998). Since minute quantities of DNA (~100 molecules) can be amplified by PCR, these selections can thus be conducted on a scale of this magnitude allowing a truly broad search for desired activities, both economical and efficient.

The display library can be selected or partitioned for binding to a target molecule. In this context, selection or partitioning means any process whereby a library member bound to a target molecule is separated from library members not bound to target molecules. Selection can be accomplished by various methods known in the art. In most applications, binding to a target molecule preferable is selective, such that the binding to the target is favored over other binding events. Ultimately, a binding molecule identified using the present invention may be useful as a therapeutic reagent and/or diagnostic agent.

The selection strategy can be carried out to allow selection against almost any target. Importantly, the selection strategy does not require any detailed structural information about the target molecule or about the members of the display library. The entire process is driven by the binding affinities and specificities involved in library members binding to a given target molecule.

Selected library members can easily be identified through their encoding nucleic acid, using standard molecular biology. The present invention broadly permits identifying binding molecules for any known target molecule. In addition, novel unknown targets can be discovered by isolating binding molecules of selected library members and use these for identification and validation of a target molecule.

Selection of binding molecules from a display library can be performed in any format to identify binding library members. Binding selection typically involves immobilizing the desired target molecule, adding the display library, allowing binding, and removing nonbinders/weak-binders by washing. The enriched library remaining bound to the target may be eluted with, for example acid, chaotropic salts, heat, competitive elution with known ligand, high salt, base, proteolytic release of target, enzymatic release of nucleic acids. In some embodiments the eluted library members are subjected to more rounds of binding and elution, using the same or more stringent conditions or using a different binding format, which will increase the enrichment. In other embodiments the binding library members are not eluted from the target. To select for library members that bind to a protein expressed on a cell surface, such as an ion channel or a transmembrane receptor, the cells themselves can be used as selection agents. A selection procedure can also involve selection for binding to cell surface receptors that are internalized so that the receptor together with the binding molecule passes into the cytoplasm, nucleus, or other cellular compartment, such as the Golgi or lysosomes. Isolation of the compartment in question leads to partitioning of library members being internalized from non-internalized library members (Hart et al., J Biol Chem, 269, 12468-74, 1994). A selection procedure may also involve in vivo selection. The enriched library's nucleic acid portion may be amplified by, for example PCR, leading to many orders of amplification, allowing identification by e.g. cloning and DNA sequencing.

According to a specific embodiment for affinity selection, a library of reaction products resulting from a specific is contacted with a target under binding conditions. If one or more of the formed chemical compounds have affinity towards the target a binding will result. In a subsequent step, binding library members or a nucleic acid derived therefrom are partitioned. The nucleic acid attached to the formed chemical compound is subsequently amplified by e.g. PCR to produce multiple copies of the nucleic acid, which codes for the synthesis history of the compound displaying the desired affinity. The amplified nucleic acid can be sequenced by a number of well-known techniques to decode which chemical groups that have participated in the formation of the successful compound. Alternatively, the amplified nucleic acid can be used for the formation of a next generation library.

EXAMPLES

Example 1

Reductive Amination

The present example serves to illustrate the possibility of effecting reductive amination within the YoctoReactor under conditions with high contents of organic solvent. As control, a comparative reaction was run in aqueous media.

Oligonucleotides were obtained from DNA Technology Arhus, Denmark, and derivatized in the following way:

Synthesis of a Benzaldehyde-Functionalized Oligo Having Internal Modified dT (amine-C6-dT; Vip046-NHCOC$_6$H$_4$—CHO).

The oligonucleotide vip046 was acylated with 4-carboxybenzaldehyde (Lancaster #8192) promoted by DMT-MM (4-(4,6-Dimethoxy-1,3,5-triazin-2-yl)-4-methylmorpholinium chloride, Fluka #74104) by treatment of the oligonucleotide (5 nmol) dissolved in a 30% DMF/water mixture containing 200 mM MOPS buffer pH 7.0 with DMT-MM 50 mM. Total reaction volume was 200 µL. The reaction was incubated for 12 hrs at 25° C. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in 100 mM TEAA buffer pH 7.0 followed by purification by HPLC and mass spectrometry analysis according to the protocol given below. Yield: 45%.

| DNA | Calculated mass | Found mass |
|---|---|---|
| vip046-NHCOC$_6$H$_4$CHO | 6729.233 | 6729.9 |

General Purification Method:

Functionalized oligonucleotides were purified by a Hewlett Packard Agilent HPLC instrument with auto sampler and fraction collector on an XTerra C18 column (Waters #186000602) using acetonitrile/TEAA 100 mM pH 7.0 mixtures as eluent. Appropriate fractions were lyophilized and diluted to 20 μM with water.

General Mass Spectrometry Analysis:

Functionalized oligonucleotides were analyzed by MALDI-TOF mass spectrometry on a Bruker AutoFlex instrument in a HPA/ammonium citrate matrix using negative ion reflector mode.

Oligonucleotides (80 pmole each of vip001, vip002, vip003, vip046-PhCHO (benzaldehyde), or vip068-NH$_2$; 20 μM stock solutions), as appropriate, were mixed with water and NaCl (Fluka #71376, 1M; final conc 70 mM) in a total of 30 μL. Solutions were subjected to an annealing programme (PCR machine: 30 sec @ 94° C., 10 sec @ 80° C., 10 sec @ 65° C., 10 sec @ 50° C., 10 sec @ 35° C., 10 sec @ 20° C., 10 sec @ 10° C.).

Solution of annealed trimer YoctoReactor or other controls were split into two portions and added 1) morpholinopropanesulfonic acid (Fluka #69947; MOPS, pH 6.0, 1M), NaCl (Fluka #71376, 4M), and water or 2) DMF, followed by sodium cyanoborohydride (240 mM, 50 μL) and acetic acid (200 mM, 20 μL) in water or DMF to a total volume of 300 μL in both reaction mixtures. Final aqueous concentrations were 1M NaCl and 100 mM MOPS buffer, pH 6.0. Final concentration of organic solvent was 95% DMF. In both reactions, final reagent concentrations were 40 mM sodium cyanoborohydride and 13 mM acetic acid. Final mixtures were incubated for 16 h at 22° C.

Reactions were quenched by EtOH precip: Added NaOAc (30 μL, 3M, Sigma #S-7899) containing approx. 540 μg/mL glycogen (Fermentas #R0561) and EtOH (1000 μL, Fluka #87047, then incubated at −18° C. for 60 min. Tubes were spun at 14000 rpm for 30 min at 4° C., supernatants removed, and the pellet dried briefly in a stream of air. Crude DNA was redissolved in water, and an aliquot of each reaction mixture was analyzed by denaturing PAGE (10%, 25% formamide, and 7M urea). Molecular marker used was Fermentas #SM1203. Bands were visualized by SYBR Green stain (Molecular Probes, #S7563) according to the manufacturer's instructions. The results can be seen in FIG. 3.

Negative controls for trimer YoctoReactor carrying only the amine or the aldehyde, but not both, did not produce any visible product, as expected (lanes 1+2 and 6+7). Trimer YoctoReactor in lanes 3 and 8 produced a clear band in both aqueous buffer and 95% DMF. The same trimer, but without added reagents, did not provide any product (lanes 4+9). Dimer YoctoReactor in lanes 5 and 10 clearly gave the highest yield when reaction was run in 95% DMF (lane 10). Thus, reductive amination appeared to work in both aqueous buffer and 95% DMF.

Example 2

Wittig Reaction

The present example serves to illustrate the possibility of effecting a Wittig reaction between an aldehyde and a phosphorane within the YoctoReactor under conditions with high contents of organic solvent. As control, a comparative reaction was run in aqueous media.

Oligonucleotides were obtained from DNA Technology Arhus, Denmark, and derivatized in the following way:

Synthesis of a Triphenylphosphonium Functionalized Oligo Having Internal Modified dT (amine-C6-dT; vip057-COCH$_2$PAr$_3$)

The oligonucleotide vip057 was acylated with SIA (N-Succinimidyl iodoacetate, Pierce #22349) at the primary amine on an internal modified dT in the oligonucleotide to yield the iodoacetamide functionalized oligo. The amino-modified oligonucleotide (5 nmol) was treated with SIA (10 mM) in a 300% DMF/water mixture containing 200 mM MOPS buffer pH 7.0. Total reaction volume was 200 μL. The reaction was incubated for 90 min at 25° C. Then, 20 μL of a 150 mM DMF solution of 4-(diphenylphosphino) benzoic acid (Aldrich#401595-1G) was added and incubated for an additional 10 hrs. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in 100 mM TEAA buffer pH 7.0 followed by purification by HPLC and mass spectrometry analysis according to Example 1. Yield: 46%.

| DNA | Calculated mass | Found mass |
|---|---|---|
| Vip057-OCH$_2$PPh$_2$PhCO$_2$H | 6962.3033 | 6957.7 |

Synthesis of a Benzaldehyde-Functionalized Oligo Having Internal Modified dT (amine-C6-dT; Vip046-NHCOC$_6$H$_4$CHO)

The oligonucleotide vip046 was acylated with 4-carboxybenzaldehyde (Lancaster #8192) promoted by DMT-MM (4-(4,6-Dimethoxy-1,3,5-triazin-2-yl)-4-methylmorpholinium chloride, Fluka #74104) by treatment of the oligonucleotide (5 nmol) dissolved in a 30% DMF/water mixture containing 200 mM MOPS buffer pH 7.0 with DMT-MM 50 mM. Total reaction volume was 200 μL. The reaction was incubated for 12 hrs at 25° C. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in 100 mM TEAA buffer pH 7.0 followed by purification by HPLC and mass spectrometry analysis according to Example 1. Yield: 45%.

| DNA | Calculated mass | Found mass |
|---|---|---|
| vip046-NHCOC$_6$H$_4$CHO | 6729.233 | 6729.9 |

Oligonucleotides (40 pmole each of vip001, vip002, vip003, vip046-PhCHO (benzaldehyde), or vip057-COCH$_2$PAr$_3$; 20 μM stock solutions) as appropriate were mixed with water and NaCl (Fluka #71376, 1M; final conc. 70 mM) in a total of 24 μL. Oligonucleotides were allowed to anneal for 10 min at ambient temperature.

Solution of annealed trimer YoctoReactor or other controls were split into two portions and added 1) morpholinopropanesulfonic acid (Fluka #69947; MOPS, pH 8.0, 1M), NaCl (Fluka #71376, 4M), and water or 2) acetonitrile, followed by sodium hydroxide (1M, 3 μL) in water to a total volume of 300 μL in both reaction mixtures. Final aqueous concentrations were 1M NaCl and 100 mM MOPS buffer, pH 8.0. Final concentration of organic solvent was 95% acetonitrile. Final mixtures were incubated for 16 h at 22° C.

Reactions were quenched by EtOH precip: Added NaOAc (30 μL, 3M, Sigma #S-7899) containing approx. 540 μg/mL glycogen (Fermentas #R0561) and EtOH (1000 μL, Fluka #87047, then incubated at −18° C. for 60 min. Tubes were spun at 14000 rpm for 30 min at 4° C., supernatants removed, and the pellet dried briefly in a stream of air. Crude DNA was redissolved in water, and an aliquot of each reaction mixture was analyzed by denaturing PAGE (10%, 25% formamide, and 7M urea). Molecular marker used was Fermentas #SM1203. Bands were visualized by SYBR Green stain (Molecular Probes, #S7563) according to the manufacturer's instructions. The results can be seen in FIG. 4.

Negative controls for trimer YoctoReactor carrying only the aldehyde or phosphorane, but not both, did not produce any visible product as expected (lanes 1+2 and 6+7). Trimer YoctoReactor in lanes 3 and 8 produced a clear band in both aqueous buffer and 95% MeCN. The same trimer, but without added sodium hydroxide, only produced a little product, thus indicating that addition of additional base besides aqueous buffer positively affected the reactions (lanes 4+9). Dimer YoctoReactor in lanes 5 and 10 clearly yielded a product yield similar to that of the full trimer. In conclusion, the Wittig reaction proceeds smoothly in both aqueous buffer and 95% MeCN. Controls appeared as would be expected for a selective reaction.

Example 3

Aldol Condensation

The present example serves to illustrate the possibility of effecting an enamine catalyzed aldol condensation within the YoctoReactor under conditions with high contents of organic solvent. As control, a comparative reaction was run in aqueous media.

Oligos were obtained from DNA Technology Arhus, Denmark, and derivatized in the following way:

Synthesis of a Ketone-Functionalized Oligo Having Internal Modified dT (amine-C6-dT; Vip057-NHCO(CH$_2$)$_3$COCH$_3$)

The oligonucleotide vip057 was acylated with 4-acetylbutyric acid (Aldrich #A1,320-4) promoted by DMT-MM (4-(4,6-Dimethoxy-1,3,5-triazin-2-yl)-4-methylmorpholinium chloride, Fluka #74104) by treatment of the oligonucleotide (5 nmol) dissolved in a 30% DMF/water mixture containing 200 mM MOPS buffer pH 7.0 with DMT-MM 50 mM. Total reaction volume was 200 μL. The reaction was incubated for 12 hrs at 25° C. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in 100 mM TEAA buffer pH 7.0 followed by purification by HPLC and mass spectrometry analysis according to Example 1. Yield: 53%.

| DNA | Calculated mass | Found mass |
|---|---|---|
| Vip057-NHCO(CH$_2$)$_3$COCH$_3$ | 6727.2733 | 6724.8 |

Preparation of Aldehyde Functionalized Oligonucleotide was Described in Example 1.

Oligonucleotides (20 pmole each of vip001, vip002, vip003, vip046-PhCHO (benzaldehyde), or vip057-COCH$_3$ (5-oxo-hexamide; 20 μM stock solutions)) as appropriate were mixed with water and NaCl (Fluka #71376, 1M; final conc 70 mM) in a total of 15 μL. Solutions were subjected to an annealing programme (PCR machine: 30 sec @ 94° C., 10 sec @ 80° C., 10 sec @ 65° C., 10 sec @ 50° C., 10 sec @ 35° C., 10 sec @ 20° C., 10 sec @ 10° C.).

Solution of annealed trimer YoctoReactor or other controls were added 1) morpholinopropanesulfonic acid (Fluka #69947; MOPS, pH 7.0, 1M), NaCl (Fluka #71376, 4M), and water or 2) acetonitrile, followed by pyrrolidine in water or acetonitrile (500 mM, 30 μL; final concentration was 50 mM) to a total volume of 300 μL in both reaction mixtures. Final aqueous concentrations were 1M NaCl and 100 mM MOPS buffer, pH 7.0. Final concentration of organic solvent was 950% acetonitrile. Final mixtures were incubated for 16 h at 22° C.

Reactions were quenched by EtOH precip: Added NaOAc (30 μL, 3M, Sigma #S-7899) containing approx. 540 μg/mL glycogen (Fermentas #R0561) and EtOH (1000 μL, Fluka #87047, then incubated at −18° C. for 60 min. Tubes were spun at 14000 rpm for 30 min at 4° C., supernatants removed, and the pellet dried briefly in a stream of air. Crude DNA was redissolved in water, and an aliquot of each reaction mixture was analyzed by denaturing PAGE (10%, 250% formamide, and 7M urea). Molecular marker used was Fermentas #SM1203. Bands were visualized by SYBR Green stain (Molecular Probes, #S7563) according to the manufacturer's instructions. The results can be seen in FIG. 5.

When reaction was run in aqueous media, it only gave a small amount of product as the intermediate imine is rapidly hydrolyzed. Thus, aqueous controls were omitted in this experiment. Negative controls for trimer YoctoReactor carrying only the aldehyde or ketone, but not both, did not produce any visible product, as expected (lanes 2+3; MeCN). Trimer YoctoReactor in lanes 4 produced a clear band in 950% MeCN. The same trimer, but without added pyrrolidine, produced no product (lane 5). Thus, pyrrolidine is essential for the reaction to proceed. Dimer YoctoReactor in lane 6 clearly yielded only a faint product band with mobility similar to that of the full trimer. In conclusion, aldol condensation appeared to work best in 950% MeCN as compared to aqueous buffer (MOPS pH 7). Controls appeared as would be expected for a selective reaction as exclusion of either reactants or catalyst quenched product formation.

Example 4

Michael Addition

The present example serves to illustrate the possibility of effecting a Michael conjugate addition within the YoctoReactor under conditions with high contents of organic solvent. As control, a comparative reaction was run in aqueous media. Maleimide or cinnamide functionalized DNA was used as acceptor in the Michael addition. As nucleophile were used both sulfur (thiol) and nitrogen (primary amine).

Oligos were obtained from DNA Technology Arhus, Denmark, and derivatized in the following way:

Synthesis of a Carboxylic Acid Functionalized Oligo Linked Through a Disulfide Bond Having Internal Modified dT (amine-C6-dT; Vip046-CO(CH$_2$)$_2$SS(CH$_2$)$_2$CO$_2$H)

The oligonucleotide vip046 was acetylated with DSP (Dithio-bis[succinimidylpropionate], Pierce #22585) at the primary amine on an internal modified dT in the oligonucleotide to yield the carboxylic acid functionalized oligo. The oligonucleotide (5 nmol) was treated with DSP (10 mM) in a 300% DMF/water mixture containing 400 mM pH 8.4 sodium phosphate buffer. Total volume of the reaction was 200 μL. The reactions were incubated for 2 hrs at 25° C. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in 100 mM TEAA buffer pH 7.0 followed by purification by HPLC and mass spectrometry analysis according to Example 1. Yield: 59%.

| DNA | Calculated mass | Found mass |
|---|---|---|
| Vip046-CO(CH$_2$)$_2$SS(CH$_2$)$_2$CO$_2$H | 6789.2020 | 6789.0 |

To produce the required DNA-linked reagent thiol reagent, disulfide was treated with 50 mM tricarboxyethylphosphine (TCEP, Fluka #93284) for 1 h at 25° C., EtOH precipitated, redissolved in water and used immediately in annealing of YoctoReactor trimer. As amine nucleophile, the internal amine modifier was used without further modification.

Synthesis of a Maleimide-Functionalized Oligo Having Internal Modified dT (amine-C6-dT; vip057-CO(CH$_2$)$_3$-maleimide)

The oligonucleotide vip057 was acylated with 4-maleimidobutyric acid (Fluka #63174) promoted by DMT-MM (4-(4, 6-Dimethoxy-1,3,5-triazin-2-yl)-4-methylmorpholinium chloride, Fluka #74104) by treatment of the oligonucleotide (5 nmol) dissolved in a 30% DMF/water mixture containing 200 mM MOPS buffer pH 7.0 with DMT-MM 50 mM. Total reaction volume was 200 μL. The reaction was incubated for 12 hrs at 25° C. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in 100 mM TEAA buffer pH 7.0 followed by purification by HPLC and mass spectrometry analysis according to Example 1. Yield: 46%.

| DNA | Calculated mass | Found mass |
|---|---|---|
| vip057-CO(CH$_2$)$_3$-maleimide | 6780.2633 | 6779.1 |

Synthesis of a Cinnamide-Functionalized Oligo Having Internal Modified dT (amine-C6-dT; vip057-COCH=CHPh)

The oligonucleotide vip057 was acylated with cinnamic acid (Aldrich #133760) promoted by DMT-MM (4-(4,6-Dimethoxy-1,3,5-triazin-2-yl)-4-methylmorpholinium chloride, Fluka #74104) by treatment of the oligonucleotide (5 nmol) dissolved in a 30% DMF/water mixture containing 200 mM MOPS buffer pH 7.0 with DMT-MM 50 mM. Total reaction volume was 200 μL. The reaction was incubated for 12 hrs at 25° C. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, New York). The pellet was resuspended in 100 mM TEAA buffer pH 7.0 followed by purification by HPLC and mass spectrometry analysis according to Example 1. Yield: 45%.

| DNA | Calculated mass | Found mass |
|---|---|---|
| vip057-COCH=CHPh | 6745.2633 | 6751.3 |

Oligonucleotides (20 pmole each of vip003, vip046-SH/NH$_2$ (thiol or amine), and vip057-maleimide/cinnamide; 20 μM stock solutions), as appropriate, were mixed with water and NaCl (Fluka #71376, 1M; final conc 70 mM) in a total of 30 μL. Oligonucleotides were allowed to anneal for 10 min at ambient temperature.

Solution of annealed trimer YoctoReactor or other controls were split into two portions and added 1) morpholinopropanesulfonic acid (Fluka #69947; MOPS, pH 8.0, 1M), NaCl (Fluka #71376, 4M), and water or 2) acetonitrile. Reaction mixture in acetonitrile was added a solution of 1% N-ethyldiisopropylamine (DIEA, 30 μL, Fluka #03440). Total volume was 300 μL in both reaction mixtures. Final aqueous concentrations were 1M NaCl and 100 mM MOPS buffer, pH 8.0. Final concentration of organic solvent was 95% acetonitrile and 0.1% DIEA. Final mixtures were incubated for 16 h at 22° C.

Reactions were quenched by EtOH precip: Added NaOAc (30 μL, 3M, Sigma #S-7899) containing approx. 540 μg/mL glycogen (Fermentas #R0561) and EtOH (1000 μL, Fluka #87047, then incubated at −18° C. for 60 min. Tubes were spun at 14000 rpm for 30 min at 4° C., supernatants removed, and the pellet dried briefly in a stream of air. Crude DNA was redissolved in water, and an aliquot of each reaction mixture was analyzed by denaturing PAGE (10%, 25% formamide, and 7M urea). Molecular marker used was Fermentas #SM1203. Bands were visualized by SYBR Green stain (Molecular Probes, #S7563) according to the manufacturer's instructions. The results can be seen in FIG. 6.

Michael additions work well for both thiol and amine nucleophiles when using maleimide as electrophile (lanes 1-4). The cinnamide is less reactive, but a weak band was observed for thiol nucleophile in MeCN (lane 6).

Example 5

Alkyne-Alkene Coupling

The present example serves to illustrate the possibility of effecting alkyne-alkene oxidative coupling (Kanan et al., Nature 2004, 431, 545-549) within the YoctoReactor under conditions with high contents of organic solvent. As control, a comparative reaction was run in aqueous media.

Oligos were obtained from DNA Technology Arhus, Denmark and derivatized in the following way:

Synthesis of an Alkene-Functionalized Oligo Having Internal Modified dT (amine-C6-dT; Vip057-CO(CH$_2$)$_2$—CH=CH$_2$)

The oligonucleotide vip057 was acylated with 4-pentenoic acid (Aldrich #245925) promoted by DMT-MM (4-(4,6-Dimethoxy-1,3,5-triazin-2-yl)-4-methylmorpholinium chloride, Fluka #74104) by treatment of the oligonucleotide (5 nmol) dissolved in a 30% DMF/water mixture containing 200 mM MOPS buffer pH 7.0 with DMT-MM 50 mM. Total reaction volume was 200 µL. The reaction was incubated for 12 hrs at 25° C. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in 100 mM TEAA buffer pH 7.0 followed by purification by HPLC and mass spectrometry analysis according to Example 1. Yield: 55%.

| DNA | Calculated mass | Found mass |
|---|---|---|
| Vip057-CO(CH$_2$)$_2$—CH=CH$_2$ | 6745.2633 | 6751.3 |

Synthesis of an Alkyne-Functionalized Oligo Having Internal Modified dT (amine-C6-dT; Vip068-CO(CH$_2$)$_4$—C≡CH)

The oligonucleotide vip068 was acylated with 6-heptynoic acid (Aldrich #442879-1G) promoted by DMT-MM (4-(4,6-Dimethoxy-1,3,5-triazin-2-yl)-4-methylmorpholinium chloride, Fluka #74104) by treatment of the oligonucleotide (5 nmol) dissolved in a 30% DMF/water mixture containing 200 mM MOPS buffer pH 7.0 with DMT-MM 50 mM. Total reaction volume was 200 µL. The reaction was incubated for 12 hrs at 25° C. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in 100 mM TEAA buffer pH 7.0 followed by purification by HPLC and mass spectrometry analysis according to Example 1. Yield: 22%.

| DNA | Calculated mass | Found mass |
|---|---|---|
| Vip068-CO(CH$_2$)$_4$—C≡CH | 6616.248 | 6616.1 |

Oligonucleotides (120 pmole each of vip001, vip057-alkene, and vip068-alkyne; 20 µM stock solutions) were mixed with water and NaCl (Fluka #71376, 1M; final conc 70 mM) in a total of 36 µL. Solution was subjected to an annealing programme (PCR machine: 30 sec @ 94° C., 10 sec @ 80° C., 10 sec @ 65° C., 10 sec @ 50° C., 10 sec @ 35° C., 10 sec @ 20° C., 10 sec @ 10° C.).

Solution of annealed trimer YoctoReactor was split into 6 portions and added either 1) morpholinopropanesulfonic acid (Fluka #69947; MOPS, pH 7.0, 1M), NaCl (Fluka #71376, 4M), and water or 2) organic solvent (acetonitrile, N-methylpyrrolidinone (NMP), or NMP containing 1% ethyldiisopropylamine (DIEA; Fluka #03440)). A 1:1 mixture of Na$_2$PdCl$_4$ (100 mM in water, Aldrich #379808) and tris(4,6-dimethyl-3-sulfanatophenyl)phosphine trisodium salt hydrate (200 mM; Strem Chemicals #15-7860, TXPTS) was incubated at ambient temperature for 15 min. All reactions were added water and aqueous catalyst/ligand as appropriate:

Reactions 1+2: Water (6 µL) and Na$_2$PdCl$_4$ (3 µL).

Reactions 3-6: Water (3 µL) and Na$_2$PdCL4/TXPTS mixture (6 µL).

Total volume was 300 µL in all reaction mixtures. Final aqueous concentrations were 1M NaCl and 100 mM MOPS buffer, pH 7.0. Final concentration of organic solvent was 95% solvent. A final concentration of Pd was 1 mM and 2 mM of TXPTS. Reaction mixtures were incubated for 16 h at 22° C.

Reactions were quenched by EtOH precip: Added NaOAc (30 µL, 3M, Sigma #S-7899) containing approx. 540 µg/mL glycogen (Fermentas #R0561) and EtOH (1000 µL, Fluka #87047, then incubated at −18° C. for 60 min. Tubes were spun at 14000 rpm for 30 min at 4° C., supernatants removed, and the pellet dried briefly in a stream of air. DNA was redissolved in 300 µL of a 20 mM DTT (Fermentas #R0861) in 2-morpholinoethanesulfonic acid (MES, pH 6, 100 mM; Fluka #69892), incubated for 10 min at 95° C., and then cooled to ambient temperature, spun for 10 min to remove precipitate, supernatant transferred to new tubes and precipitated as above. Crude DNA was redissolved in water, and an aliquot of each reaction mixture was analyzed by denaturing PAGE (10%, 25% formamide, and 7M urea). Molecular marker used was Fermentas #SM1203. Bands were visualized by SYBR Green stain (Molecular Probes, #S7563) according to the manufacturer's instructions. The result can be seen in FIG. 7.

Reactions 1-4 all four showed a clear band showing that reaction proceeds in both aqueous and organic media. However, no reaction was observed in NMP solvent mixtures. Reaction proceeded both with and without the presence of TXPTS ligand.

Example 6

Heck Reaction

The present example serves to illustrate the possibility of effecting a Heck coupling within the YoctoReactor under conditions with high content of organic solvent. As control, comparative reactions were run in aqueous media.

Oligos were obtained from DNA Technology Arhus, Denmark and derivatized in the following way:

Synthesis of an Phenyliodide-Functionalized Oligo Having Internal Modified dT (amine-C6-dT; vip046-COC$_6$H$_4$—I)

The oligonucleotide vip046 was acylated with 4-iodobenzoic acid (Merck #S35112 204) promoted by DMT-MM (4-(4,6-Dimethoxy-1,3,5-triazin-2-yl)-4-methylmorpholinium chloride, Fluka #74104) by treatment of the oligonucleotide (5 nmol) dissolved in a 30% DMF/water mixture containing 200 mM MOPS buffer pH 7.0 with DMT-MM 50 mM. Total reaction volume was 200 µL. The reaction was incubated for 12 hrs at 25° C. The crude conjugate was isolated by EtOH precipitation. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in 100 mM TEAA buffer pH 7.0 followed by purification by HPLC and mass spectrometry analysis according to Example 1. Yield: 60%.

| DNA | Calculated mass | Found mass |
|---|---|---|
| vip046-COC$_6$H$_4$—I | 6827.1320 | 6832.0 |

For preparation of 4-pentenoic acid modified oligonucleotide (vip057-alkene), see Example 5.

Oligonucleotides (20 pmole each of vip001, vip002, vip003, vip046-PhI (phenyliodide) or vip057-alkene (20 µM stock solutions)) as appropriate, were mixed with water and NaCl (Fluka #71376, 1M; final conc. 70 mM) in a total of 18 µL. Solutions were subjected to an annealing programme (PCR machine: 30 sec @ 94° C., 10 sec @ 80° C., 10 sec @ 65° C., 10 sec @ 50° C., 10 sec @ 35° C., 10 sec @ 20° C., 10 sec @ 10° C.).

Solution of annealed trimer YoctoReactor or other controls were split into two portions (9 µL each) and added 1) morpholinopropanesulfonic acid (Fluka #69947; MOPS, pH 8.0, 1M, NaCl (Fluka #71376, 4M) and water or 2) acetonitrile (Fluka #00695). A 1:1 mixture of Na$_2$PdCl$_4$ (100 mM in water, Aldrich #379808) and tris(4,6-dimethyl-3-sulfanatophenyl)phosphine trisodium salt hydrate (200 mM; Strem Chemicals #15-7860, TXPTS) was incubated at ambient temperature for 15 min. All reactions were added aqueous catalyst/ligand mixture (6 µL) except negative controls 4 and 9 where water was added. Reactions were incubated for 16 h at 37° C. Total volume was 300 µL in all reaction mixtures. Final aqueous concentrations were 1M NaCl and 100 mM MOPS buffer, pH 8.0. Final concentration of organic solvent was 95% acetonitrile. A final concentration of Pd was 1 mM and 2 mM of TXPTS.

Reactions were quenched by EtOH precip: Added NaOAc (30 µL, 3M, Sigma #S-7899) containing approx. 540 µg/mL glycogen (Fermentas #R0561) and EtOH (1000 µL, Fluka #87047, then incubated at −18° C. for 60 min. Tubes were spun at 14000 rpm for 30 min at 4° C., supernatants removed, and the pellet dried briefly in a stream of air. DNA was redissolved in 300 µL of a 20 mM DTT (Fermentas #R0861) in 2-morpholinoethanesulfonic acid (MES, pH 6, 100 mM; Fluka #69892). Incubated for 10 min at 95° C., and then cooled to ambient temperature, spun for 10 min to remove precipitate, supernatant transferred to new tubes and precipitated as above. Crude DNA was redissolved in water, and an aliquot of each reaction mixture was analyzed by denaturing PAGE (10%, 25% formamide, and 7M urea). Molecular marker used was Fermentas #SM1203. Bands were visualized by SYBR Green stain (Molecular Probes, #S7563) according to the manufacturer's instructions. The results can be seen in FIG. 8.

Negative controls for trimer YoctoReactor carrying only the phenyl iodide or alkene, but not both, did not produce any visible cross-linked material as expected (lanes 1+2 and 6+7; aqueous and MeCN, respectively). Trimer YoctoReactor in lanes 3 and 8 produced a band with a mobility of approx. 50 bp in both aqueous media and 95% MeCN. The same trimer without added Pd-catalyst produced no cross-linked material (lane 4+9). Dimer YoctoReactor in lane 6 also yielded a product band with mobility similar to that of the full trimer. Controls appeared as would be expected for a selective reaction as exclusion of either reactants or catalyst quenched product formation.

Example 7

Sonogashira Coupling

The present example serves to illustrate the possibility of effecting a Sonogashira coupling of alkynes and aryl halides within the YoctoReactor under conditions with high contents of organic solvent. As control, a comparative reaction was run in aqueous media.

Oligos were obtained from DNA Technology Arhus, Denmark, and derivatized in the following way:

For preparation of phenyliodide modified oligonucleotide, see Example 6.

For preparation of 6-heptynoic acid modified oligonucleotide, see Example 5.

Oligonucleotides (20 pmole each of vip001, vip002, vip003, vip046-PhI (phenyliodide), or vip068-alkyne (20 µM stock solutions)) as appropriate, were mixed with water and NaCl (Fluka #71376, 1M; final conc 70 mM) in a total of 6 µL. Solutions were subjected to an annealing programme (PCR machine: 30 sec @ 94° C., 10 sec @ 80° C., 10 sec @ 65° C., 10 sec @ 50° C., 10 sec @ 35° C., 10 sec @ 20° C., 10 sec @ 10° C.).

Solution of annealed trimer YoctoReactor or other controls were added 1) morpholinopropanesulfonic acid (Fluka #69947; MOPS, pH 7.0, 1M), NaCl (Fluka #71376, 4M), and water or 2) acetonitrile, followed by a 1:1 mixture (6 µL, premixed for 15 min) of Na$_2$PdCl$_4$ (100 mM in water, Aldrich #379808) and tris(4,6-dimethyl-3-sulfanatophenyl)phosphine trisodium salt hydrate (200 mM; Strem Chemicals #15-7860, TXPTS) and a 1:1 mixture (3 µL, premixed for 15 min) of CuSO$_4$ hydrate (100 mM, Riedel-de Haën #31293) and L-ascorbic acid sodium salt (1M, Fluka #11140) to a total volume of 300 µL in both reaction mixtures. Final concentrations were 1M NaCl and 100 mM MOPS buffer, pH 7.0. Final concentration of organic solvent was 95% acetonitrile. Final mixtures were incubated for 16 h at 22° C.

Reactions were quenched by EtOH precip: Added NaOAc (30 µL, 3M, Sigma #S-7899) containing approx. 540 µg/mL glycogen (Fermentas #R0561) and EtOH (1000 µL, Fluka #87047, then incubated at −18° C. for 60 min. Tubes were spun at 14000 rpm for 30 min at 4° C., supernatants removed, and the pellet dried briefly in a stream of air. DNA was redissolved in 300 µL of a 20 mM DTT (Fermentas #R0861) in 2-morpholinoethanesulfonic acid (MES, pH 6, 100 mM; Fluka #69892). Incubated for 10 min at 95° C., and then cooled to ambient temperature, spun for 10 min to remove precipitate, supernatant transferred to new tubes and precipitated as above. Crude DNA was redissolved in water, and an aliquot of each reaction mixture was analyzed by denaturing PAGE (10%, 25% formamide, and 7M urea). Molecular marker used was Fermentas #SM1203. Bands were visualized by SYBR Green stain (Molecular Probes, #S7563) according to the manufacturer's instructions. The results can be seen in FIG. 9.

Aqueous reaction in lane 1 only gave a little product as previously observed. Most of the DNA in aqueous reaction appeared to be lost, which was also observed when repeating experiment. Presumably, damage on DNA by the treatment with Cu(I) is suppressed in the organic solvent. Aqueous controls were omitted in this experiment and the following applies for reactions in acetonitrile. Negative controls for trimer YoctoReactor carrying only the phenyl iodide or alkynes but not both, did not produce any visible cross-linked material as expected (lanes 2+3; MeCN). Trimer YoctoReactor in lanes 4 produced a clear band in 95% MeCN. The same trimer without added Pd- and Cucatalysts produced no cross-linked material (lane 5). Dimer YoctoReactor in lane 6 also clearly yielded a product band with mobility similar to that of the full trimer. Sonogashira coupling proceeds most readily in 95% MeCN as compared to aqueous buffer (MOPS pH 7). Controls appeared as would be expected for a selective reaction as exclusion of either reactants or catalyst quenched product formation.

Example 8

Acylation in Polyacrylamide

The present example serves to illustrate the possibility of effecting an acylation reaction within the YoctoReactor while the trimer star structure is physically constrained within a polyacrylamide gel.

Oligonucleotides were obtained from DNA Technology Arhus, Denmark and derivatized in the following way:

General Conjugation of Amino Acids to Oligonucleotides Having Internal Modified dT (amine-C6-dT) via BSOCOES.

The oligonucleotides, vip046, vip017, vip047 and vip048, were functionalized by cross-linking an amino acid (Gly, L-Leu, L-Phe, L-Tyr, Fluka, #50052, #61820, #78020, #93829) through the alpha-amine to the primary amine on an internal modified dT in the oligonucleotide, by the homobifunctional linkers BSOCOES ((Bis[2-(succinimidooxycarbonyloxy)ethyl]sulfone), Pierce cat# 21600) by treatment of the oligonucleotide (0.5 nmol) and the amino acid (15 mM) in a 1:1 mixture of DMF and 400 mM pH 8.4 sodium phosphate buffer with the linker (10 mM). Total volume of the reactions was 20 µL. The reactions were incubated for 4 hrs at 25° C. The reaction mixture was diluted to 50 µL and purified on a spin column (Amersham Biosciences #27-5325-01) according to the manufacturer's protocol followed by purification by HPLC. Yields were determined by HPLC. Identity was determined by MALDI-TOF mass spectrometry.

| DNA | Isolated yield | Calculated mass | Found mass |
|---|---|---|---|
| vip046-BSOCOES-Gly | 32% | 6878.2325 | 6879.3 |
| vip046-BSOCOES-Leu | 48% | 6934.2951 | 6936.1 |
| vip046-BSOCOES-Phe | 49% | 6968.2795 | 6969.0 |
| vip046-BSOCOES-Tyr | 51% | 6984.2744 | 6985.5 |

General Purification Method:

Functionalized oligonucleotides were purified by a Hewlett Packard Agilent HPLC instrument with auto sampler and fraction collector on an XTerra C18 column (Waters #186000602) using acetonitrile/TEAA 100 mM pH 7.0 mixtures as eluent. Appropriate fractions were lyophilized and diluted to 20 mM with water.

General Mass Spectrometry Analysis:

Functionalized oligonucleotides were analyzed by MALDI-TOF mass spectrometry on a Bruker AutoFlex instrument in a HPA/ammonium citrate matrix using negative ion reflector mode.

Oligonucleotides (20 pmole each of vip006, vip008, vip016, vip017-Leu, or vip020; 20 mM stock solutions) as appropriate were mixed with water and NaCl (Fluka #71376, 1M; final conc 100 mM) in a total of 10 mL. The following three structures were assembled:

1) Vip006, vip017-Leu, and vip008 (trimer YoctoReactor negative control; no acceptor amine; reactions 1+6).

2) Vip020 and vip017-Leu (dimer YoctoReactor negative control; no base pairing; reactions 2+7).

3) Vip016, vip017-Leu, and vip008 (trimer YoctoReactor; reactions 3-5+8-10).

Solutions were subjected to an annealing programme (PCR machine: 30 sec @ 94° C., 10 sec @ 80° C., 10 sec @ 65° C., 10 sec @ 50° C., 10 sec @ 35° C., 10 sec @ 20° C., 10 sec @ 10° C.).

Solution of annealed trimer YoctoReactor or other controls (5 mL) in a 1.5 mL eppendorf tube was mixed with a buffer (5 mL) consisting of morpholinopropanesulfonic acid (Fluka #69947; MOPS, pH 6.5, 200 mM), NaCl (Fluka #71376, 200 mM), and water. Reaction mixtures were added 40 mL of a mixture of 30% acrylamide/bis-acrylamide (400 mL; Sigma #3449) and tetramethylenediamine (0.4 mL; TEMED, Fluka #87689) and ammonium persulfate (0.4 mL of a 10% stock; Sigma #3678). Total volume of 50 mL in all reaction mixtures. Mixtures were left to polymerize for 16 h at ambient temperature.

Pellets were washed in N-methylpyrrolidinone (NMP, 400 mL), which caused pellets to be released from tube, transferred to 2 mL tubes, and washed two more times with NMP (400 µl each, 15 min). Pellets were drained and added NMP, ethyldiisopropylamine (DIEA; Fluka #03440), and reagents (N-(3-Dimethylaminopropyl)-N'-ethylcarbodiimide (EDC; Fluka #39391), N-hydroxysuccinimide (NHS; Fluka #56480), 1-hydroxybenzotriazole (HOBt; Fluka #54802), O-(benzotriazol-1-yl)N,N,N',N'-tetramethyluronium hexafluorophosphate (HBTU, Fluka #12804), (benzotriazol-1-yloxy)tripyrrolidinophosphonium hexafluorophosphate (PyBOP, Fluka #12805)) as indicated below. Samples 6-10 were preheated to 50° C. before coupling reagent was added.

Reaction mixtures were composed as follows:

Reactions 1-3+6-8: NMP (89 mL), DIEA (1 mL), EDC (5 mL; 1M in NMP), and NHS (5 mL; 1M in NMP).

Reactions 4+9: NMP (84 mL), DIEA (1 mL), HBTU (10 mL; 0.5M in NMP), and HOBt (5 mL; 1M in NMP).

Reactions 5+10: NMP (89 mL), DIEA (1 mL), PyBOP (10 mL; 1M in NMP), and HOBt (5 mL; 1M in NMP).

Samples were agitated (800 rpm) at either 21° C., overnight (reactions 1-5) or 50° C., 1 h (reactions 6-10).

Workup procedure: Pellets were drained and washed once with NMP and twice with water (2×500 mL, 10 min each), transferred to 1.5 mL tubes and crushed. Extraction buffer was added (300 mL) and suspensions were agitated overnight at 37° C., 1400 rpm. Extraction buffer was prepared from ammonium acetate (0.5 mL, 10M NH$_4$OAc, pH 7.6), magnesium chloride (50 mL 2M MgCl$_2$, Fluka #68475), EDTA (20 mL 0.5M, pH 8.0, Fluka #03690), SDS (100 µl 100%, Fluka #71736) and diluted to 10 mL. Extraction mixtures were transferred to spin filters (Corning inc, costar, #8169), spun, and washed with another 100 mL fresh extraction buffer. Combined filtrates were added GenElute LPA (1 mL, Sigma #56575) and EtOH (1000 mL, Fluka #87047). Incubated on ice for 10 min, then spun at 14000 rpm, 4° C., 30 min. Supernatant was decanted, tube spun briefly again, remaining liquid removed by pipette, and pellet allowed to dry in a stream of air Crude DNA was redissolved in water, and each reaction mixture was analyzed by denaturing PAGE (10%, 7M urea). Molecular marker used was Fermentas #SM1203. Bands were visualized by SYBR Green stain (Molecular Probes, #S7563) according to the manufacturer's instructions. The results can be seen in FIG. 10.

No product formation was observed in either negative controls (lane 1-2+6+7). Clearly visible formation of cross-linked product in all 6 trimer reaction pellets (lanes 3-5+8–10). It appeared that PyBOP/HOBt mediated acylation gave highest yield for reaction at 21° C., whereas EDC/NHS gave the most product at 50° C. Reaction was demonstrated to be DNA directed as non-base pairing oligoes does not form product. It also appears to be specific as trimer lacking the acceptor amine does not give product.

Example 9

The purpose of this and the next example is to demonstrate the stability of the compositions of the invention in organic solvent and their ability to hybridize under such conditions. The results of these examples may serve to substantiate the definition of a solution predominantly consisting of an organic solvent as being one in which two single stranded nucleic acid strands are unable to hybridize into stems of the star structure.

Stability of Acylation Reaction in Reaction Center at Different Levels of Organic Solvent To demonstrate the stability of DNA star structures, the trans-fer of one amino acid was carried out in a mixture of $H_2O$ and an organic solvent, thus resembling conditions used in organic chemical synthesis. If base pairing and star structure were destroyed under these conditions, no cross-linked product could be formed. The solvents dioxane, acetonitrile, and tetrahydrofurane were chosen with regard to miscibility with water and general applicability in organic synthesis.

Figure 11:
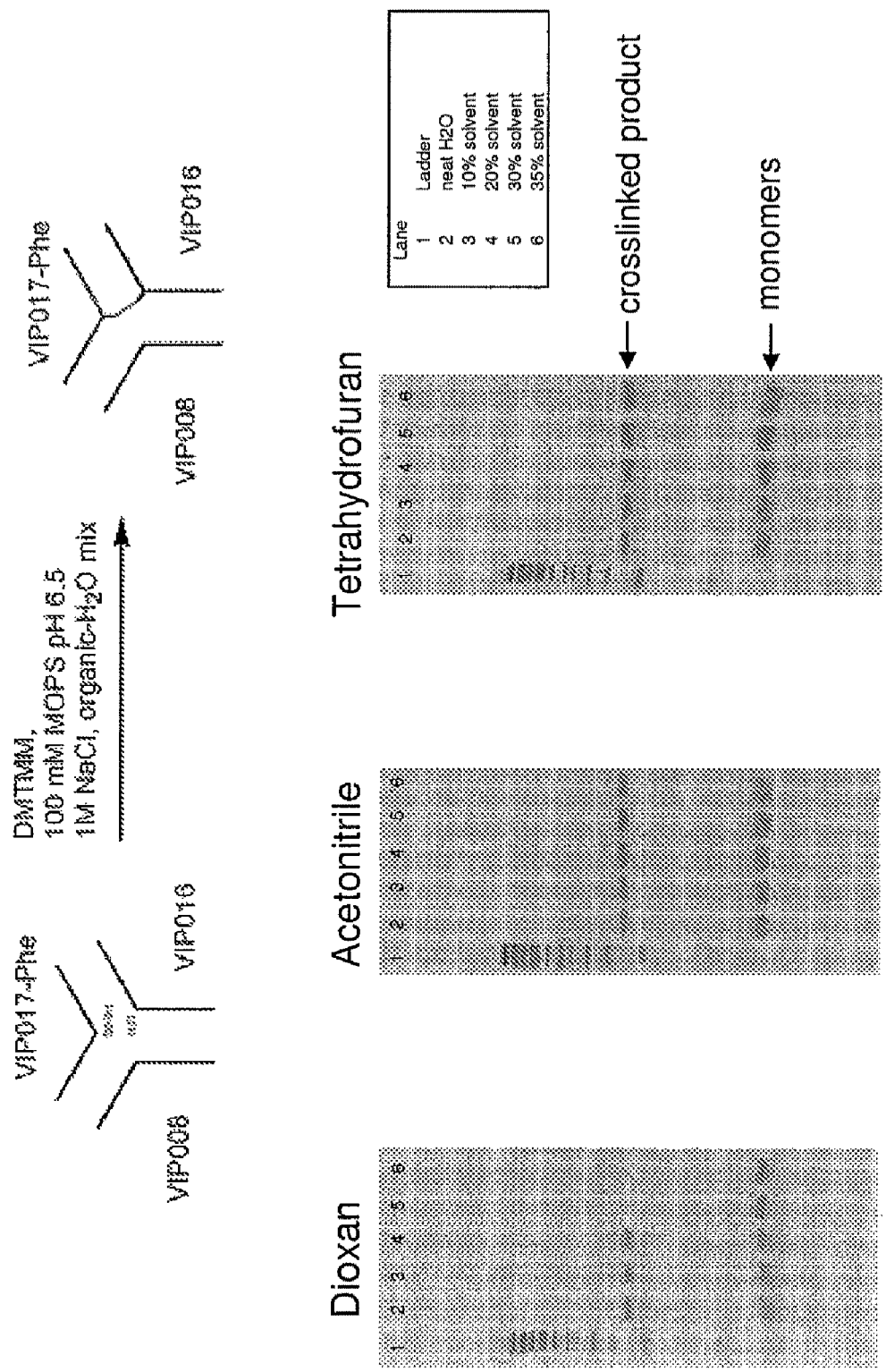
FIG. 11 shows a gel from an experiment reported in example 9.

Oligos vip016, vip008, and vip017-Phe (DNA Technology Arhus, Denmark, vip017 derivatized as described in example 11) as 20 μM stock solutions were mixed in a buffer of MOPS (200 mM, pH 6.5; Fluka #69947) and NaCl (2M; Fluka #71376), and subjected to an annealing programme (PCR machine: 5 min @ 94° C., 30 sec @ 80° C., 30 sec @ 65° C., 30 sec @ 50° C., 30 sec @ 35° C., 30 sec @ 20° C., 30 sec @ 10° C.). This annealing mixture was diluted into mixtures of solvent and water to a final composition of morpholinopropanesulfonic acid (MOPS, 100 mM, pH 6.5), NaCl (1M), solvent (0, 10, 20, 30, or 35 vol %), and chemical activator (DMTMM, Fluka #74104, 1.0M aq. sol, final concentration of 75 mM), which was incubated at 50° C. for 1 h. Final DNA concentration was 0.5 μM. Reaction mixtures were analyzed by denaturing PAGE (10% gel), which was stained with SYBR green (Molecular Probes, #S7563) according to the manufacturer's instructions. The results are shown in FIG. 11.

For dioxane, cross-linked product was formed with up to 20% solvent. On the other hand, for all reactions containing acetonitrile or tetrahydrofuran, similar amounts of product were formed, thus indicating that the presence of at least up to 35% of the organic solvent was well tolerated and DNA base pairing was intact.

Example 10

Stability of Reaction Center at Different Levels of DMF

To demonstrate the stability of DNA star structures, the transfer of one amino acid was carried out in a $H_2O$-DMF mixture, thus resembling conditions used in organic chemical synthesis. If base pairing and star structure were destroyed under these conditions, no cross-linked product could be formed.

Figure 12:
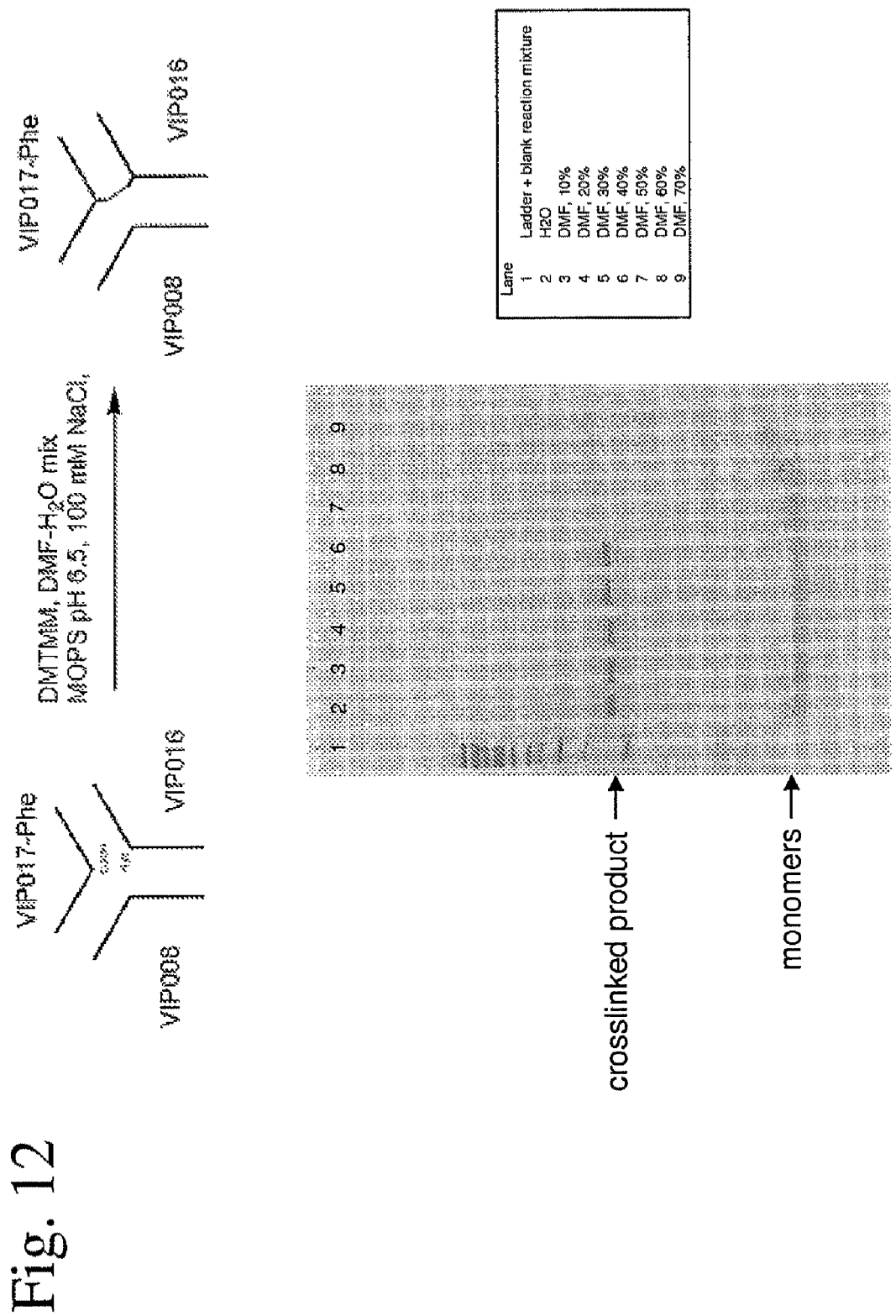
FIG. 12 shows a gel from an experiment reported in example 10.

Oligos vip016, vip008, and vip017-Phe (DNA Technology Arhus, Denmark, vip017 derivatized as described in example 11) as 20 μM stock solutions were mixed in a buffer of MOPS (500 mM, pH 6.5; Fluka #69947) and NaCl (4M; Fluka #71376), and subjected to an annealing programme (PCR machine: 5 min @ 94° C., 30 sec @ 80° C., 30 sec @ 65° C., 30 sec @ 50° C., 30 sec @ 35° C., 30 sec @ 20° C., 30 sec @ 10° C.). This annealing mixture was diluted into mixtures of DMF and water to a final composition of morpholinopropanesulfonic acid (MOPS, 12.5 mM, pH 6.5), NaCl (100 mM), DMF (0, 10, 20, 30, 40, 50, 60, or 70 vol % DMF), and chemical activator (DMTMM, Fluka #74104, 1.0M aq. sol, final concentration of 75 mM), which was incubated overnight at 25° C. Final DNA concentration was 0.5 μM. Reaction mixtures were analyzed by denaturing PAGE (10% gel), which was stained with SYBR green (Molecular Probes, #S7563) according to the manufacturer's instructions. The results are shown in FIG. 12.

The product band produced in the first five lanes was of similar intensity, thus indicating that the presence of at least up to 40% of the organic solvent, DMF, was well tolerated and DNA base pairing was intact. At 50% DMF, a weak band was still observed, but from 60% and above no cross-linked product was detected.

List of oligonucleotides used in the examples:

| Name | Sequence | Length | Modification |
|---|---|---|---|
| vip001 | ACCGACTCTGGAAGTGTCACCGGATCTGG | 29 | |
| vip002 | CCAGATCCGGTGACTGTCAAGGCTGAGGT | 29 | |
| vip003 | ACCTCAGCCTTGACTCTTCCAGAGTCGGT | 29 | |
| vip006 | CTCGTTTTCGAGACCGACTCTGGAAGTGTCACCGGATCTGG | 41 | |
| vip008 | GAGgGAGAGcCTCACCTCAGCCTTGACTCTTCCAGAGTCGGT | 42 | |
| vip016 | CTCGTTTTCGAGACCGACTCTGGAAGnGTCACCGGATCTGG | 41 | n = amine-C6-dT |
| vip017 | TTGGAAAAAcCAACCAGATCCGGTGACnGTCAAGGCTGAGGT | 42 | n = amine-C6-dT |
| vip020 | ACACAAGAAGTGTAGAATGCGTTCTCCnCTTCCAGAGTCGGT | 42 | n = amine-C6-dT |
| vip046 | ACTCTGGAAGnGTCACCGGAT | 21 | n = amine-C6-dT |
| vip057 | ATCCGGTGACnGTCAAGGCTG | 21 | n = amine-C6-dT |
| vip068 | CAGCCTTGACnCTTCCAGAGT | 21 | n = amine-C6-dT |

The invention claimed is:
1. A method for preparing compounds by nucleic acid directed synthesis, comprising the steps of:
   (i) preparing an aqueous solution comprising a composition forming a star structure defining 3 or more stems extending from a reaction center, each stem being formed by a nucleic acid duplex and at least 2 chemical groups being attached in or in the vicinity of the reaction center;
   (ii) transferring the composition to a solution comprising 70% (V/V) or more of an organic solvent;
   (iii) providing, in the solution obtained in step (ii), conditions under which the at least 2 chemical groups undergo reaction, thus providing a chemical compound.

2. The method according to claim 1, further comprising the step (ia) between step (i) and step (ii) of providing in the solution obtained in step (i) conditions under which the at least 2 chemical groups will undergo reaction, thus providing a chemical compound.

3. The method according to claim 1, wherein the stems are connected by means of joints extendable by an enzyme.

4. The method according to claim 3, wherein the extendable joints are naturally occurring nucleic acids whereto a chemical group is optionally attached via a linker.

5. The method according to claim 1, wherein a loop is present at all extremes of the stems except one, so as to form a contiguous nucleic acid sequence.

6. The method according to claim 1, wherein at least one of the chemical groups is attached to the extendable joints by a linker.

7. The method according to claim 6, wherein at least one of the chemical groups is attached via a linker that is not cleavable under conditions where the linker(s) attaching the remaining chemical group(s) is/are cleaved.

8. The method according to claim 6, wherein at least one of the chemical groups is attached directly to at least one of the extendable joints.

9. The method according to claim 1, wherein the composition forming a star structure has 4 stems.

10. The method according to claim 1, wherein the solution of step (ii) is obtained by pouring an organic solvent to the aqueous solution obtained in step (i).

11. The method according to claim 1, wherein the solution obtained in step (ii) does not contain a quaternary ammonium salt.

12. The method according to claim 1, wherein the solution obtained in step (ii) comprises between 70 and 99.9% (V/V) of an organic solvent.

13. The method according to claim 1, wherein the solution obtained in step (ii) comprises between 70 and 99% (V/V) of an organic solvent.

14. The method according to claim 1, wherein the solution obtained in step (ii) comprises between 90 and 99% (V/V) of an organic solvent.

15. The method according to claim 1, wherein the organic solvent is miscible with water.

16. The method according to claim 13, wherein the organic solvent is selected from the group consisting of acetonitrile, DMF, THF, dioxane, N-methylpyrrolidinone (NMP), dimethylacetamide (DMA), formamide, nitromethane, methanol, ethanol, propanol, tert-butanol, dimethylsulfoxide (DMSO), ethylene glycol, acetone, 2,2,2-trifluoroethanol (TFE), hexafluoro-2-propanol, sulfolane, 2-propanol, 1-butanol, 2-butanol, tetrahydropyran, nitroethane, 2-butanone, 2-methoxyethanol and ethylene glycol dimethyl ether.

17. The method according to claim 1, wherein the organic solvent is immiscible with water.

18. The method according to claim 17, wherein the organic solvent is selected from dichloromethane, chloroform, 1,2-dichloroethane, tetrachloromethane, toluene, benzene, ethyl acetate, propionitrile, diethylether, methyl tert-butyl ether (MTBE) and alkanes (e.g. pentane, hexane, heptane).

19. The method according to claim 1, wherein the reaction of step (iii) involves a reactant that is not associated with the reaction center, the reactant being essentially immiscible in water and/or involved in the reaction through a water-incompatible mechanism.

20. The method according to claim 1, wherein the reaction of step (iii) comprises Wittig and related reactions, Aldol condensations, Heck reactions, alkene-alkyne oxidative couplings, reductive amination and amine acylation reactions.

21. The method according to claim 1, wherein the reaction of step (iii) comprises Michael addition or Sonogashira coupling.

22. The method according to claim 1, wherein the conditions provided in step (iii) are selected from adjustment of pH, temperature, pressure, salt concentration and addition of further reactants not associated with the reaction center.

23. The method according to claim 1, wherein at least one of the chemical groups attached in or in the vicinity of the reaction center is a chemical compound obtained by the method according to any of the preceding claims.

24. The method according to claim 1, wherein the chemical compound obtained in step (iii) is formed by means of 2 or more reaction steps.

25. The method according to claim 1, wherein the chemical compound obtained in step (iii) is attached to a single joint extendable by an enzyme.

26. The method according to claim 1, comprising the further step of performing an enzymatic extension reaction to display the chemical compound formed.

27. A composition comprising a nucleic acid and at least 2 chemical groups attached to the nucleic acid, said composition forming a star structure defining 3 or more stems extending from a reaction center, each stem being formed of a nucleic acid duplex and the chemical groups being located in the reaction center, and wherein the chemical groups can react only in a solution comprising 70% (V/V) or more of an organic solvent.

28. A composition comprising a nucleic acid and a chemical compound, said composition forming a star structure defining 3 or more stems extending from a reaction center, each stem being formed of a nucleic acid duplex, wherein the chemical compound has been formed in the reaction center as a product, the product being obtainable by reacting at least 2 chemical groups in a solution comprising 70% (V/V) or more of an organic solvent.

29. The composition according to claim 28, wherein the chemical compound is covalently associated with the nucleic acid.

30. The composition according to claim 28, wherein the chemical compound is formed by reaction of the chemical groups attached to the nucleic acid and optionally one or more further reactants.

31. The composition according to claim 29, wherein the chemical compound is formed by reaction of the chemical groups attached to the nucleic acid and optionally one or more further reactants.

32. The composition according to claim 30, wherein the one or more reactants are free reactants not associated with a nucleic acid.

33. The composition according to claim 31, wherein the one or more reactants are free reactants not associated with a nucleic acid.

34. A library of compositions comprising a plurality of compositions according to claim 28.

35. A method for obtaining a library of compositions comprising collecting a plurality of compositions obtained by the method of claim 1.

36. A method for preparing compounds by nucleic acid directed synthesis, comprising the steps of:
(i) preparing an aqueous solution comprising a composition forming a first stem of a star structure extending from a reaction center, the stem being formed by a nucleic acid duplex, wherein a chemical group is attached to each of the nucleic acid strands forming the duplex;
(ii) providing conditions under which the 2 chemical groups undergo reaction, thus providing a chemical compound or intermediate;
(iii) adding to the composition obtained in step (ii) a third nucleic acid strand forming at least a second stem of a star structure extending from a reaction center, the stem being formed by a nucleic acid duplex, wherein a chemical group is attached to the third nucleic acid strand;
(iv) providing, in the composition obtained in step (iii), conditions under which the chemical group and the compound or intermediate obtained in step (ii) will undergo reaction, thus providing a chemical compound or intermediate;
wherein at least one of the steps (ii) or (iv) is performed in a solution comprising 70% (V/V) or more of an organic solvent.

37. The method according to claim 36, wherein the third nucleic acid strand added in step (iii) forms a second and third stem, thus resulting in a star structure having three stems.

38. The method according to claim 36 further comprising the steps of:
(v) adding to the composition obtained in step (iv) a fourth nucleic acid strand forming a third and fourth stem of a star structure extending from a reaction center formed by nucleic acid duplexes, wherein a chemical group is attached to the fourth nucleic acid strand;
(vi) providing, in the composition obtained in step (v), conditions under which the chemical group and the compound or intermediate obtained in step (iv) will undergo reaction, thus providing a chemical compound;
wherein at least one of the steps (ii), (iv) or (vi) is performed in a solution predominantly consisting of an organic solvent.

39. The method according to claim 36, wherein a loop is present at all extremes of the stems except one, so as to form a contiguous nucleic acid sequence.

40. The methods according to claim 36, comprising the further step of performing an enzymatic extension reaction to display the chemical compound formed.

\* \* \* \* \*